US008119129B2

(12) United States Patent
Jure-Kunkel et al.

(10) Patent No.: US 8,119,129 B2
(45) Date of Patent: Feb. 21, 2012

(54) COMBINATION OF ANTI-CTLA4 ANTIBODY WITH DASATINIB FOR THE TREATMENT OF PROLIFERATIVE DISEASES

(75) Inventors: Maria Jure-Kunkel, Plainsboro, NJ (US); Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/462,168

(22) Filed: Jul. 30, 2009

(65) Prior Publication Data

US 2010/0098701 A1 Apr. 22, 2010

Related U.S. Application Data

(60) Provisional application No. 61/085,466, filed on Aug. 1, 2008, provisional application No. 61/226,910, filed on Jul. 20, 2009.

(51) Int. Cl.
*A61K 39/395* (2006.01)
(52) U.S. Cl. .................................................. 424/130.1
(58) Field of Classification Search .................. None
See application file for complete search history.

(56) References Cited

U.S. PATENT DOCUMENTS

| 5,811,097 | A | 9/1998 | Allison et al. |
| 5,855,887 | A | 1/1999 | Allison et al. |
| 5,977,318 | A | 11/1999 | Linsley et al. |
| 6,011,029 | A | 1/2000 | Ding et al. |
| 6,051,227 | A | 4/2000 | Allison et al. |
| 6,207,156 | B1 | 3/2001 | Kuchroo et al. |
| 6,262,094 | B1 | 7/2001 | Hoeffe et al. |
| 6,682,736 | B1 | 1/2004 | Hanson et al. |
| 6,984,720 | B1 | 1/2006 | Korman et al. |
| 7,132,281 | B2 | 11/2006 | Hanson et al. |
| 7,465,446 | B2 | 12/2008 | Lowry et al. |
| 2002/0039581 | A1 | 4/2002 | Carreno et al. |
| 2002/0086014 | A1 | 7/2002 | Korman et al. |
| 2004/0241169 | A1 | 12/2004 | Lowy et al. |
| 2005/0201994 | A1 | 9/2005 | Korman et al. |
| 2006/0235006 | A1 | 10/2006 | Lee et al. |
| 2009/0074752 | A1 | 3/2009 | Lowy et al. |
| 2009/0074787 | A1 * | 3/2009 | Gomez-Navarro et al. ........... 424/142.1 |
| 2009/0149510 | A1 | 6/2009 | Hangauer et al. |
| 2009/0286782 | A1 * | 11/2009 | Ibrahim et al. ........... 514/234.2 |
| 2010/0278828 | A1 | 11/2010 | Jure-Kunkel |

FOREIGN PATENT DOCUMENTS

| EP | 1262193 A1 | 12/2002 |
| EP | 1212422 B1 | 2/2007 |
| WO | WO9842752 | 10/1998 |
| WO | WO0037504 | 6/2000 |
| WO | WO0114424 A2 | 3/2001 |
| WO | WO03086459 A1 | 10/2003 |
| WO | WO2004009769 A2 | 1/2004 |
| WO | WO2004015130 A2 | 2/2004 |
| WO | WO2004035607 A2 | 4/2004 |
| WO | WO2005003298 A2 | 1/2005 |
| WO | WO2006028999 P2 | 3/2006 |
| WO | WO2006048749 A1 | 5/2006 |
| WO | WO2006101692 A1 | 9/2006 |
| WO | WO2006113304 A2 | 10/2006 |
| WO | WO2006121168 A1 | 11/2006 |
| WO | WO2007008463 A2 | 1/2007 |
| WO | WO2007056539 A2 | 5/2007 |
| WO | WO2007056540 A2 | 5/2007 |
| WO | WO2007067959 A2 | 6/2007 |
| WO | WO2007113648 A2 | 10/2007 |
| WO | WO2008030611 A2 | 3/2008 |
| WO | WO2008121307 A2 | 10/2008 |
| WO | WO2009046407 A2 | 4/2009 |
| WO | WO2009/089260 A2 | 7/2009 |
| WO | WO2009089260 A2 | 7/2009 |
| WO | WO2010014784 A2 | 2/2010 |
| WO | WO2011/011027 A1 | 1/2011 |

OTHER PUBLICATIONS

LeTourneau et al., Cancer Treatment Reviews (2008) 34: 37-48.*
Bashey, et al., "Phase I Study of a Neutralizing Monoclonal Anti-CTLA4 Antibody (MDX-010) In Patients With Relapse of Malignancy After Allogeneic Hematopoietic Stem Cell Transplantation", Biology of Blood and Marrow Transplantation, Kluge Cargen Jennings Publishing, Charlottesville, VA, vol. 11, No. 2 (2005).
Morris, et al., "Department of Defense Prostate Cancer Clinical Trials Consortium: A New Instrument for Prostate Cancer Clinical Research", Clinical Genitourinary Cancer, vol. 7 (1), pp. 51-57 (2009).
Korman, et al. "Tumor immunotherapy: Preclinical and clinical activity of anti-CTLA4 antibodies", Curr. Opinion Invest. Drugs, vol. 6 (6), pp. 582-591 (2005).
Masters, et al., "Antitumor Activity of Cytotoxic T-lymphocyte Antigen-4 Blockade Alone or Combined with Paclitaxel, Etoposide, or Gemcitabine in Murine Models", J. Immunother, (Abstracts) vol. 32 (9.), pp. 994 (2009).
Lynch, et al., "Phase II trial of ipilimumab (IPI) and paclitaxel/carboplatin (P/C) in first-line stage IIIb/IV non-small cell lung cancer (NSCLC)", J. Clin Oncol. 28:15s, 2010 (suppl; abstr 7531); 2010 ASCO Annual Meeting, Abstract No. 7531.
Lynch, et al., "Phase II trial of ipilimumab (IPI) and paclitaxel/carboplatin (P/C) in first-line stage IIIb/IV non-small cell lung cancer (NSCLC)", Abstract 375 PD—Study CA184-041, publication Oct. 12, 2010.
Lynch, et. al, Overall Survival (OS) and Progression Free Survival (PFS) Results For A Randomized Phase 2 Trial of Ipilimumab (IPI) and Paclitaxel/Carboplatin (P/C) in First-Line Stage IIIB/IV Non-Small Cell Lung Cancer (NSCLC), vol. 21, Supplement 8, Annals of Oncology (375PD), 2010.

* cited by examiner

*Primary Examiner* — Ilia Ouspenski
(74) *Attorney, Agent, or Firm* — Stephen C. D'Amico

(57) ABSTRACT

Compositions and methods are disclosed which are useful of the treatment and prevention of proliferative disorders.

11 Claims, 9 Drawing Sheets

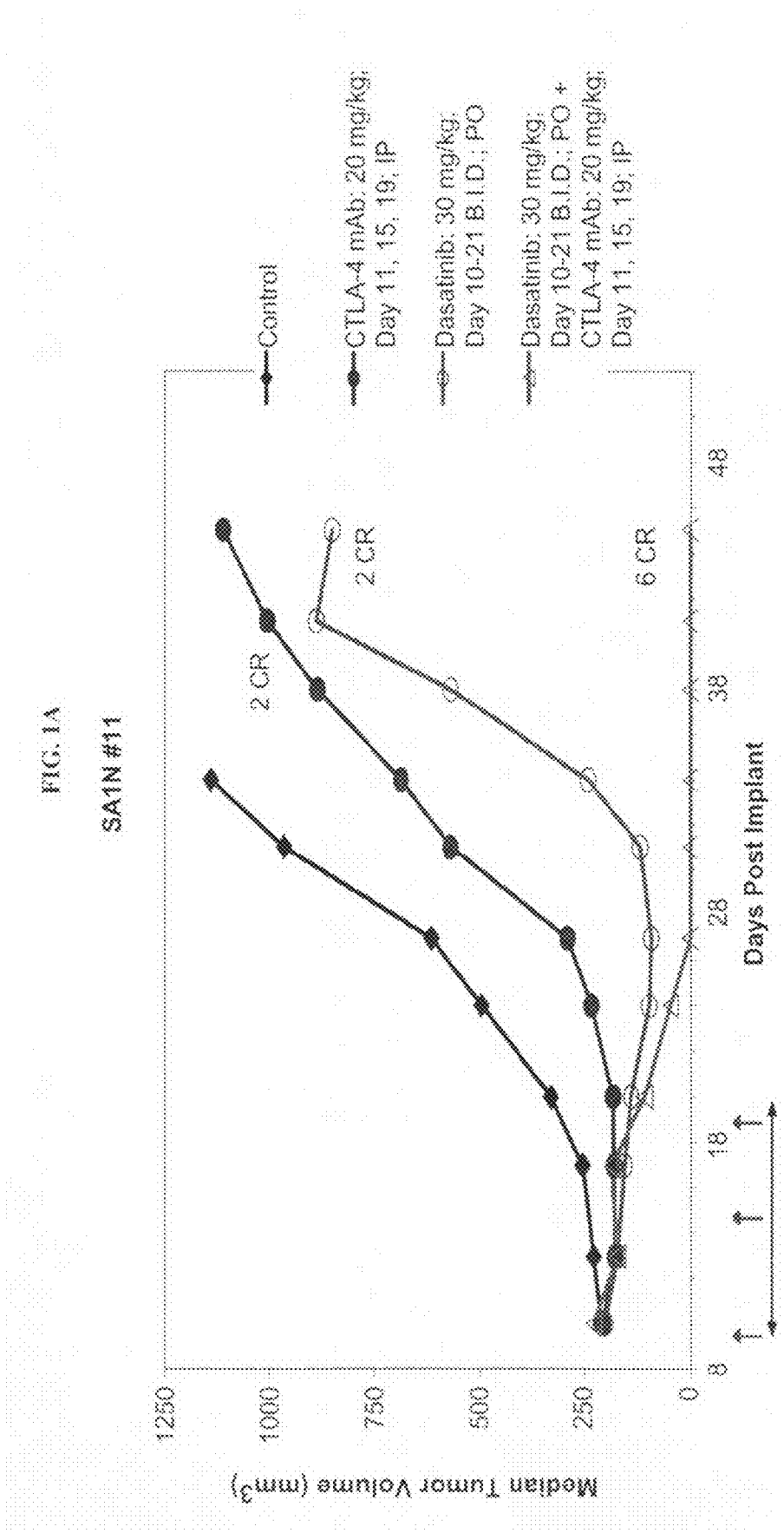

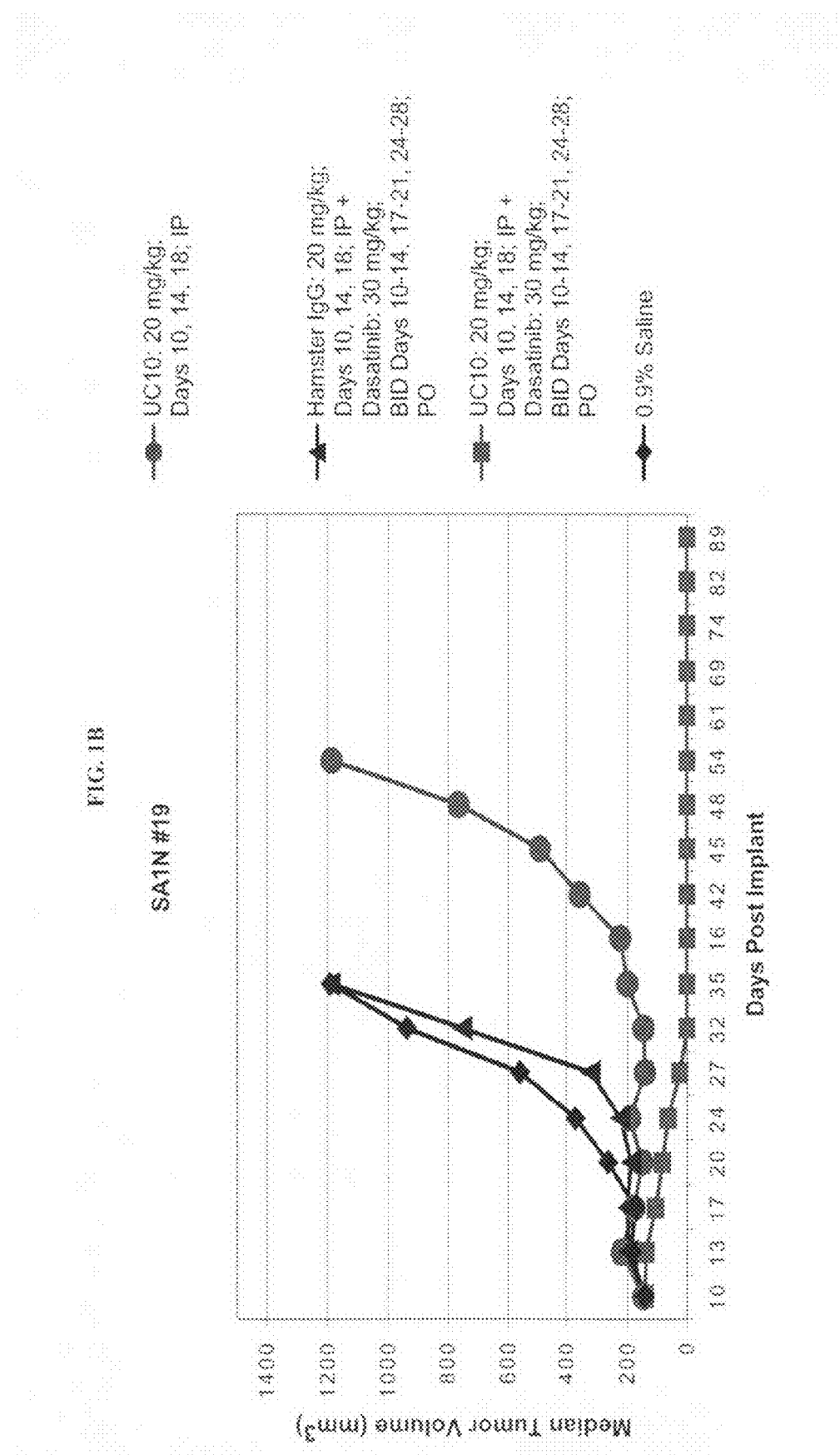

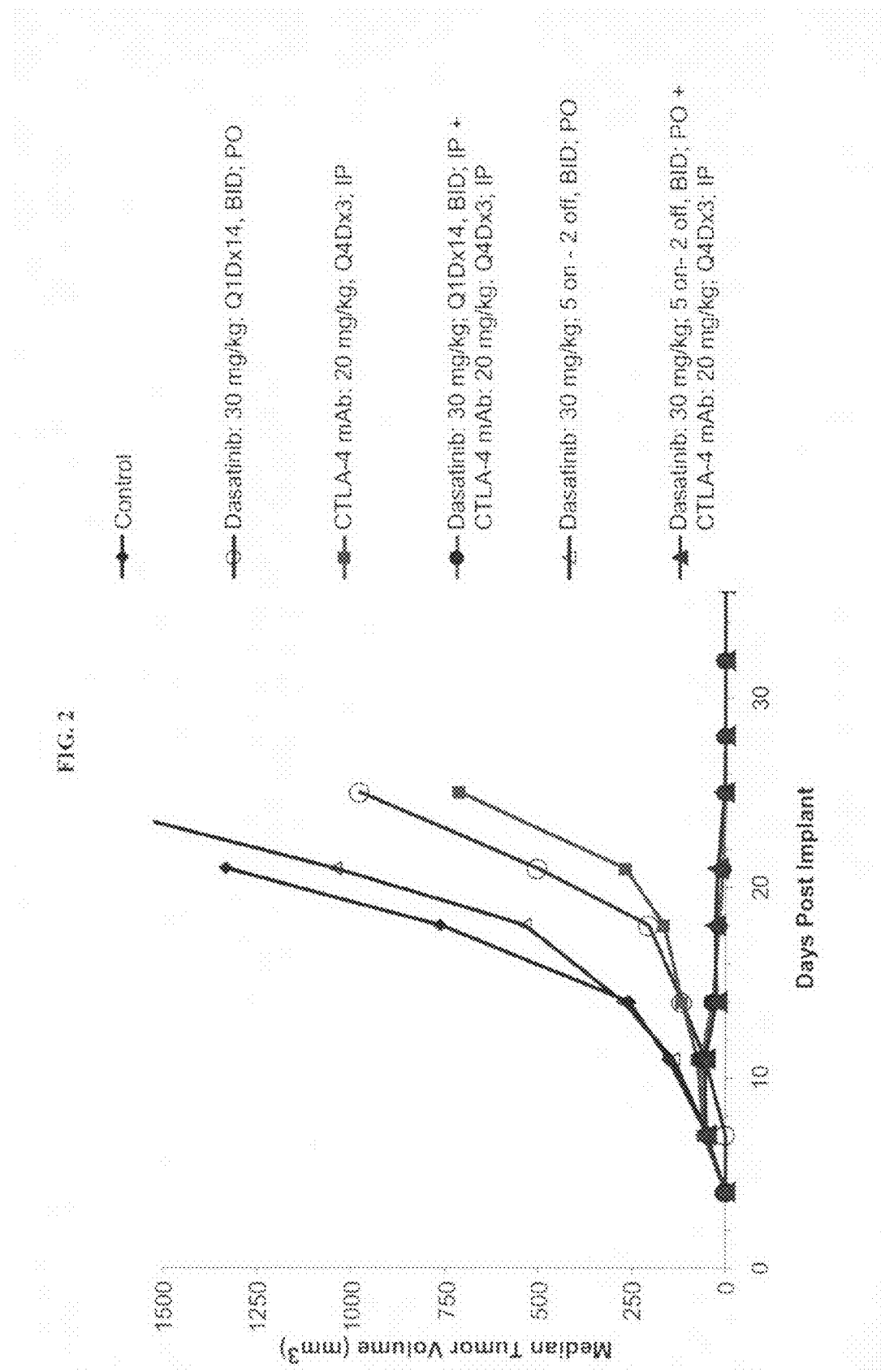

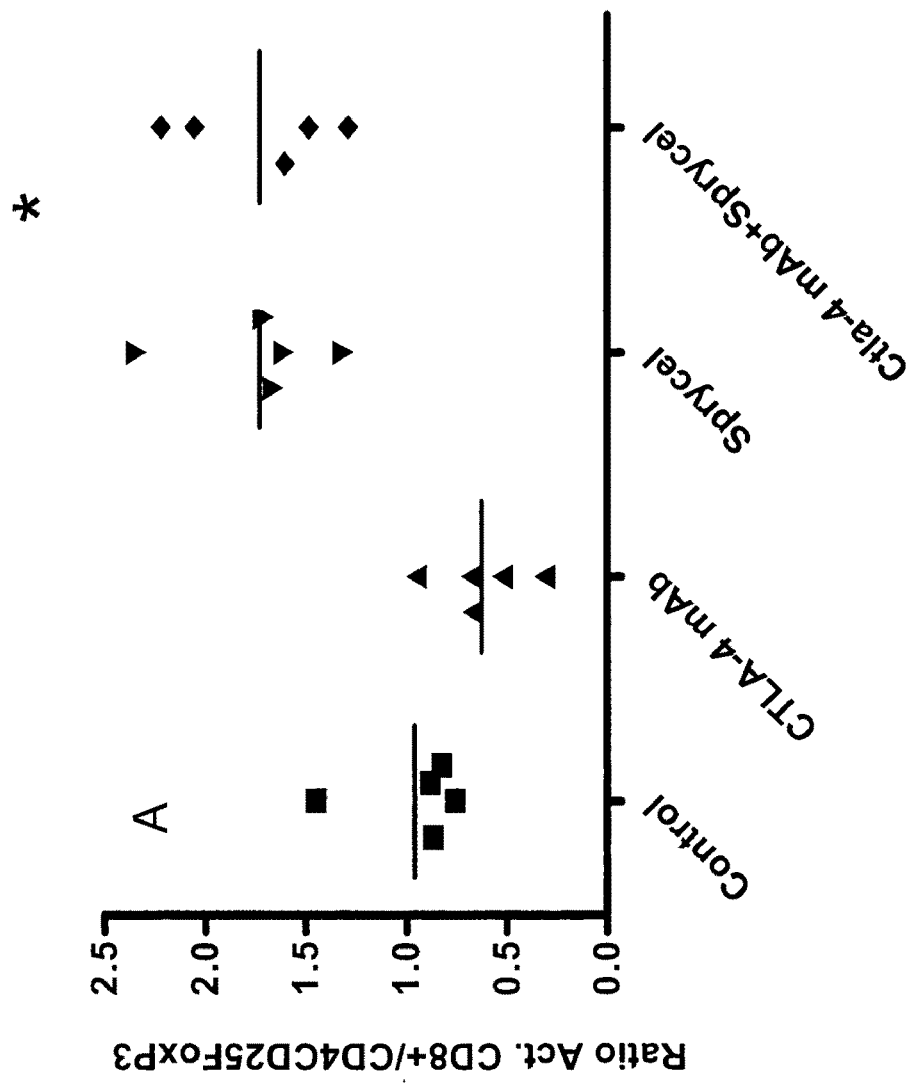

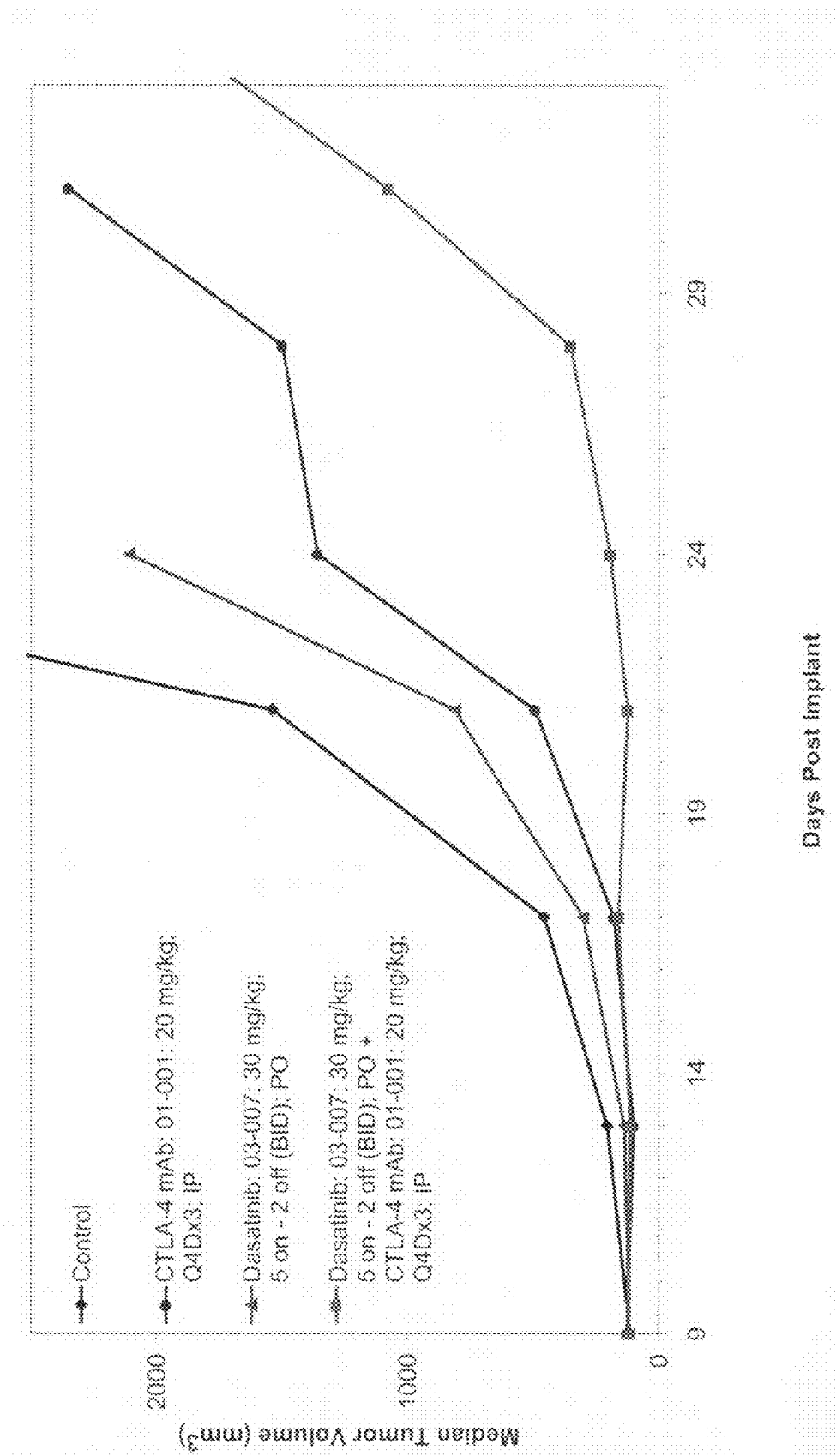

SEQUENCE LISTING

```
<160> NUMBER OF SEQ ID NOS: 4

<210> SEQ ID NO 1
<211> LENGTH: 108
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 2
<211> LENGTH: 118
<212> TYPE: PRT
<213> ORGANISM: Homo sapiens
```

```
<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 3
<211> LENGTH: 9
<212> TYPE: PRT
<213> ORGANISM: Homo sapiens

<400> SEQUENCE: 3

Ile Met Asp Gln Val Pro Phe Ser Val
1               5

<210> SEQ ID NO 4
<211> LENGTH: 9
<212> TYPE: PRT
<213> ORGANISM: Homo sapiens

<400> SEQUENCE: 4

Tyr Leu Glu Pro Gly Pro Val Thr Val
1               5
```

COMBINATION OF ANTI-CTLA4 ANTIBODY WITH DASATINIB FOR THE TREATMENT OF PROLIFERATIVE DISEASES

This application claims benefit to provisional application U.S. Ser. No. 61/085,466, filed Aug. 1, 2008; and to provisional application U.S. Ser. No. 61/226,910, filed Jul. 20, 2009; under 35 U.S.C. 119(e). The entire teachings of the referenced applications are incorporated herein by reference.

FIELD OF THE INVENTION

This invention relates to the fields of oncology and improved therapy regimens.

BACKGROUND OF THE INVENTION

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromatase inhibitors, bifunctional alkylating agents, etc.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

Ipilimumab is a human anti-human CTLA-4 antibody which blocks the binding of CTLA-4 to CD80 and CD86 expressed on antigen presenting cells and thereby, blocking the negative downregulation of the immune responses elicited by the interaction of these molecules. Since ipilimumab does not recognize mouse CTLA-4, an anti-mouse CTLA-4 antibody (clone UC10-4F10) was used in the studies presented here to investigate the effect of CTLA-4 blockade with chemotherapeutic agents.

Dasatinib (SPRYCEL®) is commonly used for the treatment of many types of cancer and represent an attractive class of agents to combine with CTLA-4 blockade.

Microtubule-stabilizing agents, such as ixabepilone (IXEMPRA™) and paclitaxel (TAXOL®), are commonly used for the treatment of many types of cancer and represent an attractive class of agents to combine with CTLA-4 blockade.

Nucleoside analogues, such as gemcitabine, are also commonly used for the treatment of many types of cancers. Gemcitabine is an antimetabolite nucleoside analogue (2',2'-difluorodeoxycytidine) that becomes active after intracellular phosphorylation by deoxycytidine kinase as only its di- and tri-phosphate forms possess cytotoxic activity. Specifically, the triphosphate form competes with deoxycytidine triphosphate for incorporation into DNA as an inactive base, and the diphosphate form inhibits ribonucleotide reductase, an enzyme that is essential for normal DNA synthesis.

Gemcitabine has been studied in a wide variety of malignancies, both as single agent and in combination with other cytotoxic drugs. Moreover it is approved in many countries for the treatment of a variety of neoplasms in man, including pancreatic, ovarian, non-small cell lung, bladder and breast carcinoma. Its therapeutic use in these tumors is also supported by a favorable toxicity profile.

Another common mechanism of inhibiting cancer cells is to induce double stranded DNA breaks. Such DNA breaks specifically kill rapidly dividing cells such as cancer cells. Etoposide is a cancer drug that induces strand breaks in cellular DNA by inhibiting topoisomerase II (topoII) religation of cleaved DNA molecules. Although DNA cleavage by topoisomerase II always produces topoisomerase II-linked DNA double-strand breaks (DSBs), the action of etoposide also results in single-strand breaks (SSBs), since religation of the two strands are independently inhibited by etoposide.

In the studies described herein, the combination of dasatinib, paclitaxel, etoposide, and gemcitabine individually with a CTLA-4 inhibitor were investigated in several tumor models with different sensitivity to each agent.

The present inventors have discovered for the first time the synergistic benefit of combining a protein tyrosine kinase inhibitor, such as dasatinib, with an anti-CTLA-4 inhibitor for the treatment of proliferative diseases. In addition, the present inventors have discovered for the first time the synergistic benefit of combining a microtubuline-stabilizing agent, such as paclitaxel, with an anti-CTLA-4 inhibitor for the treatment of proliferative diseases. In addition, the present inventors have discovered for the first time the synergistic benefit of combining a nucleoside analogue, such as gemcitabine, with an anti-CTLA-4 inhibitor for the treatment of proliferative diseases. Furthermore, the present inventors have discovered for the first time the synergistic benefit of combining a DNA double strand inducing agent, such as etoposide, with an anti-CTLA-4 inhibitor for the treatment of proliferative diseases. It is an object of the invention to provide efficacious combination chemotherapeutic treatment regimens wherein one or more of the following: a protein tyrosine kinase inhibitor, a microtubuline-stabilizing agent, a nucleoside analogue, or a DNA double strand inducing agent is combined with one or more anti-CTLA4 agents for the treatment of proliferative diseases.

SUMMARY OF THE INVENTION

The present invention provides a synergistic method for the treatment of anti-proliferative diseases, including cancer, which comprises administering to a mammalian species in need thereof a synergistic, therapeutically effective amount of: (1) a member of the group consisting of: a protein tyrosine kinase inhibitor, such as dasatinib, a microtubuline-stabilizing agent, such as paclitaxel; a nucleoside analogue, such as gemcitabine; or a DNA double strand inducing agent, such as etoposide; and (2) a co-stimulatory pathway modulator, such as an anti-CTLA4 antagonist.

In one aspect, the proliferative disease is one or more cancerous solid tumors such as lung cancer, pancreatic cancer, colon cancer, prostate cancer, and/or CML or leukemia. In another aspect, the proliferative disease is one or more refractory tumors. In yet another aspect, the CTLA-4 antibody is ipilimumab or tremelimumab. In another aspect, the protein tyrosine kinase inhibitor is SPRYCEL®, GLEEVEC®, or nilotinib. In another aspect, the microtubulin-stabilizing agent is paclitaxel, TAXOL®, epothilone A, epothilone B, epothilone C, epothilone D, or ixabepilone. In another aspect, the nucleoside analogue is gembitabine. In another aspect, the DNA double strand inducing agent is etoposide, calicheamicin, bleomycin, neocarzinostatin, sulforaphane, or idarubicin. In another aspect, a nucleoside analogue is gemcitabine, BCH-4556, clofarabine, fludarabine, cladribine, cytarabine, puromycin, and fluorouracil.

Suitable anti-CTLA4 antagonist agents for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., *Proc. Natl. Acad. Sci. USA*, 95(17):10067-10071 (1998); Camacho et al., *J. Clin. Oncology*, 22(145): Abstract No. 2505 (2004) (antibody CP-675206); Mokyr et al., *Cancer Res.*, 58:5301-5304 (1998), and U.S. Pat. Nos. 5,977,318, 6,682,736, 7,109,003, and 7,132,281.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

Each of these references is specifically incorporated herein by reference for purposes of description of CTLA-4 antibodies. A preferred clinical CTLA-4 antibody is human monoclonal antibody 10D1 (also referred to as MDX-010 and ipilimumab and available from Medarex, Inc., Bloomsbury, N.J.) is disclosed in WO 01/14424.

BRIEF DESCRIPTION OF THE DRAWINGS

FIG. 1A-1B illustrates results showing that concurrent treatment with CTLA-4 mAb and dasatinib produced synergistic effects in the SA1N fibrosarcoma tumor model. Dasatinib was administered daily for 11 days ("A") or for 15 days following an intermittent schedule (5 days on/2 days off) ("B").

FIG. 2 illustrates results showing that concurrent treatment with dasatinib and CTLA-4 mAb produced synergistic effects in the CT-26 tumor model.

FIG. 4A-4B illustrates results showing that combinatorial treatment with dasatinib and CTLA-4 mAb results in an increase in the ratio of CD8 activated T cells (CD8+CD69+, T effector cells) over A) T regulatory cells (CD4+CD25+ FoxP3+, T suppressor cells) and B) Activated CD4+T cells in tumor-draining lymph nodes (TDLN). Mice bearing subcutaneous CT26 colon tumors were treated with dasatinib (30 mg/kg, q1dx14, bid, days 4-18 after tumor cell implantation), CTLA-4 mAb (20 mg/kg, q4dx3, days 4, 8, 12 after tumor cell implantation) or the combination of both agents. TDLN were collected 2 days after the final treatment, and subjected to immunophenotypic characterization by flow cytometry.

FIG. 5 illustrates that concurrent treatment with SPRYCEL® and CTLA-4 mAb produced enhanced effects in a P815 tumor model. SPRYCEL® was administered P.O. on days 9-13, 16-20, 23-27 post tumor implantation where as anti-CTLA-4 mAb was dosed IP on days 10, 14, 18.

DETAILED DESCRIPTION OF THE INVENTION

Figure 3A:
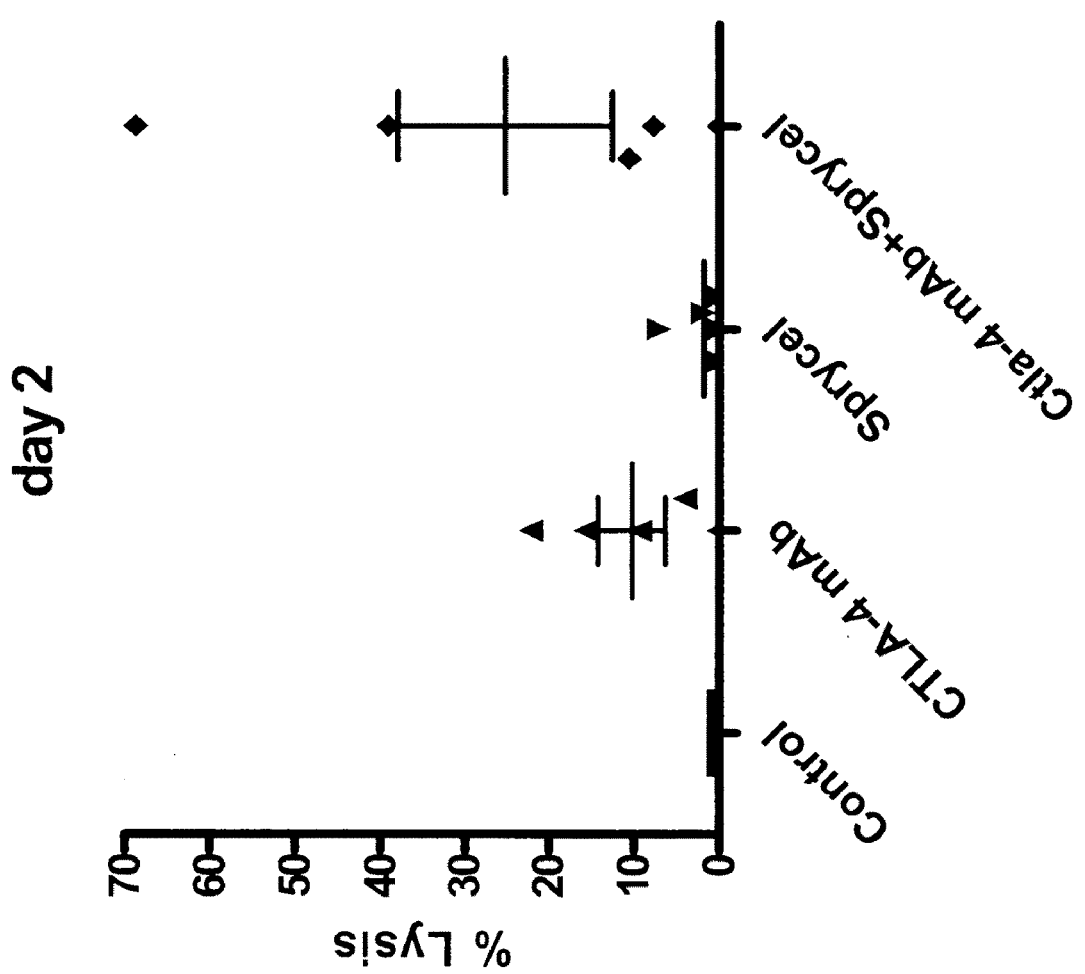
FIG. 3A-3C illustrates results showing that treatment with dasatinib augments the cytolytic activity of CTLA-4 mAb. Mice bearing subcutaneous CT26 colon tumors were treated with dasatinib (30 mg/kg, q1dx14, bid, days 4-18 after tumor cell implantation), CTLA-4 mAb (20 mg/kg, q4dx3, days 4, 8, 12 after tumor cell implantation) or the combination of both agents. Two (A), 7 (B) and 14 (C) days after the final treatment, mice (n=5/group) were injected with CFSE-labeled syngeneic splenocytes pulsed with CT26-specific peptides (AH-1). Eighteen hours later, splenocytes were isolated and cytolytic activity was determined by measuring the ratio of CFSE-labeled cells (CFSE high=peptide pulsed, CFSE low=not pulsed). Combination of dasatinib and CTLA-4 showed enhancement of peptide-pulsed splenocyte lysis which reached statistical significance by day 14 (p=0.055).

The present invention provides a synergistic method for the treatment of anti-proliferative diseases, including cancer, which comprises administering to a mammalian species in need thereof a synergistic, therapeutically effective amount of: (1) a member of the group consisting of: a protein tyrosine kinase inhibitor, such as dasatinib, a microtubuline-stabilizing agent, such as paclitaxel; a nucleoside analogue, such as gemcitabine; or a DNA double strand inducing agent, such as etoposide; and (2) a co-stimulatory pathway modulator, such as an anti-CTLA4 antagonist.

Optimal T cell activation requires interaction between the T cell receptor and specific antigen (Bretscher, P. et al., *Science*, 169:1042-1049 (1970)) (the first signal) and engagement of costimulatory receptors on the surface of the T cell with costimulatory ligands expressed by the antigen-presenting cell (APC) (the second signal). Failure of the T cell to receive a second signal can lead to clonal anergy (Schwartz, R. H., *Science*, 248:1349-1356 (1990)). Two important T cell costimulatory receptors are CD28 and cytotoxic T lymphocyte-associated antigen 4 (CTLA-4, CD152) whose ligands on APC are B7-1 and B7-2 (Linsley, P. S. et al., *J. Exp. Med.*, 173:721-730 (1991); Linsley, P. S. et al., *J. Exp. Med.*, 174: 561-569 (1991)). Although CD28 and CTLA-4 are closely related members of the Ig superfamily (Brunet, J. F. et al., *Nature*, 328:267-270 (1987)), they function antagonistically. CD28 is constitutively expressed on the surface of T cells (Gross, J. A. et al., *J. Immunol.*, 149:380-388 (1992)), and upon engagement with B7-1 or B7-2, enhances the T cell receptor-peptide-MHC signal to promote T cell activation, proliferation, and IL-2 production (Linsley, P. S. et al., *J. Exp. Med.*, 173:721-730 (1991); Alegre, M. L. et al., *Nat. Rev. Immunol.*, 1(3):220-228 (December 2001)). CTLA-4 is not found on resting T cells but is up-regulated for 2-3 days after T cell activation (Lindsten, T. et al., *J. Immunol.*, 151:3489-3499 (1993); Walunas, T. L. et al., *Immunity*, 1, 405-413 (1994)). CTLA-4 also binds to B7-1 and B7-2 but with greater affinity than CD28 (Linsley, P. S. et al., *Immunity*, 1:793-801 (1994)) and antagonizes T cell activation, interferes with IL-2 production and IL-2 receptor expression, and interrupts cell cycle progression of activated T cells (Walunas, T. L. et al., *J. Exp. Med.*, 183:2541-2550 (1996); Krummel, M. F. et al., *J. Exp. Med.*, 183:2533-2540 (1996); Brunner, M. C. et al., *J. Immunol.*, 162:5813-5820 (1999); Greenwald, R. J. et al., *Eur. J. Immunol.*, 32:366-373 (2002)). The overall T cell response is determined by the integration of all signals, stimulatory and inhibitory.

Because CTLA-4 appears to undermine T cell activation, attempts have been made to block CTLA-4 activity in murine models of cancer immunotherapy. In mice implanted with immunogenic tumors, administration of anti-CTLA-4 Ab enhanced tumor rejection (Leach, D. R. et al., *Science*, 271: 1734-1736 (1996)), although little effect was seen with poorly immunogenic tumors such as SM1 mammary carcinoma or B16 melanoma. Enhanced antitumor immunity was seen when anti-CTLA-4 Ab was given with granulocyte-macrophage colony-stimulating factor (GM-CSF)-transduced B16 cell vaccine and was associated with depigmentation, suggesting that at least part of the antitumor response was antigen-specific against "self" melanocyte differentiation antigens (van Elsas, A. et al., *J. Exp. Med.*, 190:355-366 (1999); van Elsas, A. et al., *J. Exp. Med.*, 194:481-489 (2001)). In a transgenic murine model of primary prostate cancer, administrating anti-CTLA-4 Ab plus GM-CSF-expressing prostate cancer cells reduced the incidence and histological severity of prostate cancer and led to prostatitis in normal mice, again suggesting an antigen-specific immune response against self-antigens in tumor rejection (Hurwitz, A. A. et al., *Cancer Res.*, 60:2444-2448 (2000)). Furthermore, because many human tumor antigens are normal self-antigens, breaking tolerance against self may be critical to the success of cancer immunotherapy. The favorable tumor responses from CTLA-4 blockade in conjunction with tumor vaccines in murine models led to interest in using CTLA-4 blockade in human cancer immunotherapy.

Chemoimmunotherapy, the combination of chemotherapeutic and immunotherapeutic agents, is a novel approach for the treatment of cancer which combines the effects of agents that directly attack tumor cells producing tumor cell necrosis or apoptosis, and agents that modulate host immune responses to the tumor. Chemotherapeutic agents could enhance the effect of immunotherapy by generating tumor antigens to be presented by antigen-presenting cells creating a "polyvalent" tumor cell vaccine, and by distorting the tumor architecture, thus facilitating the penetration of the immunotherapeutic agents as well as the expanded immune population.

Thus, the present invention provides methods for the administration of a protein tyrosine kinase inhibitor in synergistic combination(s) with at least one anti-CTLA4 agent for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, bone cancer, bone tumors, adult malignant fibrous histiocytoma of bone; childhood malignant fibrous histiocytoma of bone, sarcoma, pediatric sarcoma, sinonasal natural killer, neoplasms, plasma cell neoplasm; myelodysplastic syndromes; neuroblastoma; testicular germ cell tumor, intraocular melanoma, myelodysplastic syndromes; myelodysplastic/myeloproliferative diseases, synovial sarcoma, chronic myeloid leukemia, acute lymphoblastic leukemia, philadelphia chromosome positive acute lymphoblastic leukemia (Ph+ ALL), multiple myeloma, acute myelogenous leukemia, chronic lymphocytic leukemia, mastocytosis and any symptom associated with mastocytosis, and any metastasis thereof. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, mast cell leukemia, in addition to other cancers. Other cancers are also included within the scope of disorders including, but are not limited to, the following: carcinoma, including that of the bladder, urothelial carcinoma, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma, and any metastasis thereof. Preferably, such methods of treating cancer with the treatment regimens of the present invention will result in a diminished incidence of anti-CTLA agent-induced colitis.

The combination of a protein tyrosine kinase inhibitor with at least one co-stimulatory pathway modulator, preferably an anti-CTLA4 agent, may also include the addition of an anti-proliferative cytotoxic agent. Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

For the purposes of the present invention, a co-stimulatory pathway modulator encompasses one or more of the following: an anti-CTLA4 agent, an anti-CTLA-4 antibody, ipilimumab, and tremelimumab.

Other co-stimulatory pathway modulators of the present invention that may be used in combination with a protein tyrosine kinase inhibitor, either alone or in further combination with other co-stimulatory pathway modulators disclosed herein, or in combination with other compounds disclosed herein include, but are not limited to, the following: agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70; B7-1, B7-2, ICAM-1, ICAM-2, ICAM-3, CD48, LFA-3, CD30 ligand, CD40 ligand, heat stable antigen, B7h, OX40 ligand, LIGHT, CD70 and CD24.

In a preferred embodiment of this invention, a method is provided for the synergistic treatment of cancerous tumors. Advantageously, the synergistic method of this invention reduces the development of tumors, reduces tumor burden, or produces tumor regression in a mammalian host.

The combination of a protein tyrosine kinase inhibitor, such as dasatinib, a microtubuline-stabilizing agent, such as paclitaxel; a nucleoside analogue, such as gemcitabine; or a DNA double strand inducing agent, such as etoposide, with at least one anti-CTLA4 agent, may also include the addition of an anti-proliferative cytotoxic agent either alone or in combination with radiation therapy.

Other anti-proliferative cytotoxic agents are navelbene, CPT-11, anastrazole, letrazole, capecitabine, reloxafine, cyclophosphamide, ifosamide, and droloxafine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as TAXOL®), Mithramycin, Deoxycoformycin, Mitomycin-C, L-Asparaginase, Interferons (especially IFN-a), Etoposide, and Teniposide.

Other combinations with the at least one co-stimulatory pathway modulator, preferably an anti-CTLA4 agent, may include a combination of a co-stimulatory pathway agonist (i.e., immunostimulant), a tubulin stabilizing agent (e.g., pacitaxol, epothilone, taxane, etc.), IXEMPRA™, Dacarbazine, PARAPLATIN®, Docetaxel, one or more peptide vaccines, MDX-1379 Melanoma Peptide Vaccine, one or more gp100 peptide vaccine, fowlpox-PSA-TRICOM™ vaccine, vaccinia-PSA-TRICOMT™ vaccine, MART-1 antigen, sargramostim, tremelimumab, Combination Androgen Ablative Therapy; the combination of ipilimumab and another co-stimulatory pathway agonist; combination of ipilimumab and a tubulin stabilizing agent (e.g., pacitaxol, epothilone, taxane, etc.); combination of ipilimumab and IXEMPRA™, the combination of ipilimumab with Dacarbazine, the combination of ipilimumab with PARAPLATIN®, the combination of ipilimumab with Docetaxel, the combination of ipilimumab with one or more peptide vaccines, the combination of ipilimumab with MDX-1379 Melanoma Peptide Vaccine, the combination of ipilimumab with one or more gp100 peptide vaccine, the combination of ipilimumab with fowlpox-PSA-TRICOM™ vaccine, the combination of ipilimumab with vaccinia-PSA-TRICOM™ vaccine, the combination of ipilimumab with MART-1 antigen, the combination of ipilimumab with sargramostim, the combination of ipilimumab with tremelimumab, and/or the combination of ipilimumab with Combination Androgen Ablative Therapy. The combinations of the present invention may also be used in conjunction with other well known therapies that are selected for their particular usefulness against the condition that is being treated.

The phrase "radiation therapy" includes, but is not limited to, x-rays or gamma rays which are delivered from either an externally applied source such as a beam or by implantation of small radioactive sources.

As used in this specification and the appended Claims, the singular forms "a", "an", and "the" include plural referents unless the content clearly dictates otherwise. Thus, for example, reference to "a peptide" includes a combination of two or more peptides, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As is known in the art, dasatinib is also referred to as N-(2-chloro-6-methylphenyl)-2-[[6-[4-(2-hydroxyethyl)-1-piperazinyl]-2-methyl-4-pyrimidinyl]amino]-5-thiazolecarboxamide and describes a compound having the following structure (I):

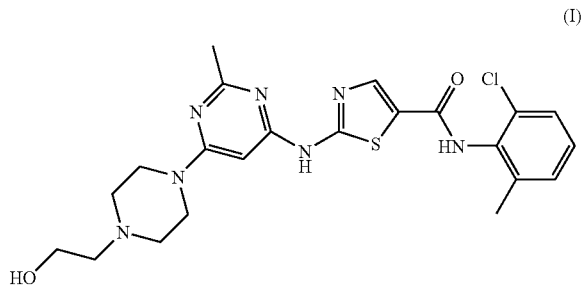

Compound (I) can also be referred to as N-(2-chloro-6-methylphenyl)-2-((6-(4-(2-hydroxyethyl)-1-piperazinyl)-2-methyl-4-pyrimidinyl)amino)-1,3-thiazole-5-carboxamide in accordance with IUPAC nomenclature. Use of the term "N-(2-chloro-6-methylphenyl)-2-[[6-[4-(2-hydroxyethyl)-1-piperazinyl]-2-methyl-4-pyrimidinyl]amino]-5-thiazole-carboxamide" encompasses (unless otherwise indicated) solvates (including hydrates) and polymorphic forms of the compound (I) or its salts (such as the monohydrate form of (I) described in U.S. Ser. No. 11/051,208, filed Feb. 4, 2005, incorporated herein by reference in its entirety and for all purposes). Pharmaceutical compositions of N-(2-chloro-6-methylphenyl)-2-[[6-[4-(2-hydroxyethyl)-1-piperazinyl]-2-methyl-4-pyrimidinyl]amino]-5-thiazolecarboxamide include all pharmaceutically acceptable compositions comprising N-(2-chloro-6-methylphenyl)-2-[[6-[4-(2-hydroxyethyl)-1-piperazinyl]-2-methyl-4-pyrimidinyl]amino]-5-thiazolecarboxamide and one or more diluents, vehicles and/or excipients, such as those compositions described in U.S. Ser. No. 11/402,502, filed Apr. 12, 2006, incorporated herein by reference in its entirety and for all purposes. One example of a pharmaceutical composition comprising N-(2-chloro-6-methylphenyl)-2-[[6-[4-(2-hydroxyethyl)-1-piperazinyl]-2-methyl-4-pyrimidinyl]amino]-5-thiazolecarboxamide is SPRYCEL® (Bristol-Myers Squibb Company). SPRYCEL® comprises N-(2-chloro-6-methylphenyl)-2-[[6-[4-(2-hydroxyethyl)-1-piperazinyl]-2-methyl-4-pyrimidinyl]amino]-5-thiazolecarboxamide as the active ingredient, also referred to as dasatinib, and as inactive ingredients or excipients, lactose monohydrate, microcrystalline cellulose, croscarmellose sodium, hydroxypropyl cellulose, and magnesium stearate in a tablet comprising hypromellose, titanium dioxide, and polyethylene glycol.

It is to be understood that this invention is not limited to particular methods, reagents, compounds, compositions, or biological systems, which can, of course, vary. It is also to be understood that the terminology used herein is for the purpose of describing particular aspects only, and is not intended to be limiting.

As is known in the art, Ipilimumab refers to an anti-CTLA-4 antibody, and is a fully human IgG$_{1R}$ antibody derived from transgenic mice having human genes encoding heavy and light chains to generate a functional human repertoire. Ipilimumab can also be referred to by its CAS Registry No. 477202-00-9, and is disclosed as antibody 10DI in PCT Publication No. WO 01/14424, incorporated herein by reference in its entirety and for all purposes. Specifically, Ipilimumab describes a human monoclonal antibody or antigen-binding portion thereof that specifically binds to CTLA4, comprising a light chain variable region and a heavy chain variable region having a light chain variable region comprised of SEQ ID NO:5, and comprising a heavy chain region comprised of SEQ ID NO:6. Pharmaceutical compositions of Ipilimumab include all pharmaceutically acceptable compositions comprising Ipilimumab and one or more diluents, vehicles and/or excipients. Examples of a pharmaceutical composition comprising Ipilimumab are provided in PCT Publication No. WO 2007/67959. Impilimumab may be administered by I.V.

Light chain variable region for Impilimumab:

(SEQ ID NO: 5)
EIVLTQSPGTLSLSPGERATLSCRASQSVGSSYLAWYQQKPGQAPRLLI

YGAFSRATGIPDRFSGSGSGTDFTLTISRLEPEDFAVYYCQQYGSSPWTF

GQGTKVEIK

Heavy chain variable region for Impilimumab:

(SEQ ID NO: 6)
QVQLVESGGGVVQPGRSLRLSCAASGFTFSSYTMHWVRQAPGKGLEWVTF

ISYDGNNKYYADSVKGRFTISRDNSKNTLYLQMNSLRAEDTAIYYCART

GWLGPFDYWGQGTLVTVSS

As noted elsewhere herein, the administration of one or more anti-CTLA4 antagonists may be administered either alone or in combination with a peptide antigen (e.g., gp100), in addition to an anti-proliferative agent disclosed herein. A non-limiting example of a peptide antigen would be a gp100 peptide comprising, or alternatively consisting of, the sequence selected from the group consisting of: IMDQVPFSV (SEQ ID NO:1), and YLEPGPVTV (SEQ ID NO:2). Such a peptide may be administered orally, or preferably by injection s.c. at 1 mg emulsified in incomplete Freund's adjuvant (IFA) injected s.c. in one extremity, and 1 mg of either the same or a different peptide emulsified in IFA may be injected in another extremity.

As is known in the art, paclitaxel refers to a compound having the following structure

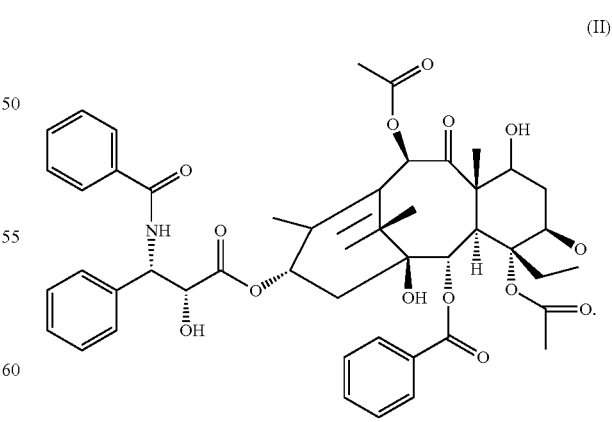

Compound (II) can also be referred to as 5beta,20-Epoxy-1,2alpha,4,7beta,10beta,13alpha-hexahydroxytax-11-en-9-one 4,10-diacetate 2-benzoate 13-ester with (2R,3S)-N-benzoyl-3-phenylisoserine in accordance with IUPAC nomenclature. Use of the term "5beta,20-Epoxy-1,2alpha,4, 7beta,10beta,13alpha-hexahydroxytax-11-en-9-one 4,10-diacetate 2-benzoate 13-ester with (2R,3S)—N-benzoyl-3-phenylisoserine" encompasses (unless otherwise indicated) solvates (including hydrates) and polymorphic forms of the compound (II) or its salts, such as the forms of (II) described in U.S. Pat. No. 5,504,102, issued Apr. 2, 1996, incorporated herein by reference in its entirety and for all purposes. Pharmaceutical compositions of 5beta,20-Epoxy-1,2alpha,4, 7beta,10beta,13alpha-hexahydroxytax-11-en-9-one 4,10-diacetate 2-benzoate 13-ester with (2R,3S)—N-benzoyl-3-phenylisoserine include all pharmaceutically acceptable compositions comprising 5beta,20-Epoxy-1,2alpha,4,7beta, 10beta,13alpha-hexahydroxytax-11-en-9-one 4,10-diacetate 2-benzoate 13-ester with (2R,3S)—N-benzoyl-3-phenylisoserine and one or more diluents, vehicles and/or excipients. One example of a pharmaceutical composition comprising 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine is TAXOL® (Bristol-Myers Squibb Company). TAXOL® comprises 5beta,20-Epoxy-1,2alpha,4,7beta,10beta,13alpha-hexahydroxytax-11-en-9-one 4,10-diacetate 2-benzoate 13-ester with (2R,3S)—N-benzoyl-3-phenylisoserine as the active ingredient, also referred to as paclitaxel, for IV infusion including inactive ingredients in the form of a diluent consisting of a sterile 0.9% Sodium Chloride injection, USP, 5% Dextrose Injection, USP, 0.9% Sodium Chloride and 5% Dextrose Injection, USP, or 5% Dextrose in Ringer's Injection to a final concentration of 0.3 to 1.2 mg/ml.

As is known in the art, gemcitabine refers to a compound having the following structure (III):

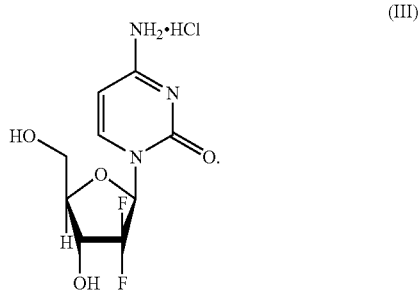

(III)

Compound (III) can also be referred to as 2'-deoxy-2',2'-difluorocytidine monohydrochloride (β-isomer) in accordance with IUPAC nomenclature. Use of the term "2'-deoxy-2',2'-difluorocytidine monohydrochloride (β-isomer)" encompasses (unless otherwise indicated) solvates (including hydrates) and polymorphic forms of the compound (III) or its salts. Pharmaceutical compositions of 2'-deoxy-2',2'-difluorocytidine monohydrochloride (β-isomer) and one or more diluents, vehicles and/or excipients. One example of a pharmaceutical composition comprising 2'-deoxy-2',2'-difluorocytidine monohydrochloride β-isomer) is GEMZAR® (gemcitabine HCl). GEMZAR® comprises 2'-deoxy-2',2'-difluorocytidine monohydrochloride (β-isomer) as the active ingredient, for IV infusion including inactive ingredients in a sterile form for intravenous use only. Vials of GEMZAR® contain either 200 mg or 1 g of gemcitabine HCl (expressed as free base) formulated with mannitol (200 mg or 1 g, respectively) and sodium acetate (12.5 mg or 62.5 mg, respectively) as a sterile lyophilized powder. Hydrochloric acid and/or sodium hydroxide may have been added for pH adjustment.

As is known in the art, etoposide refers to a compound having the following structure (IV):

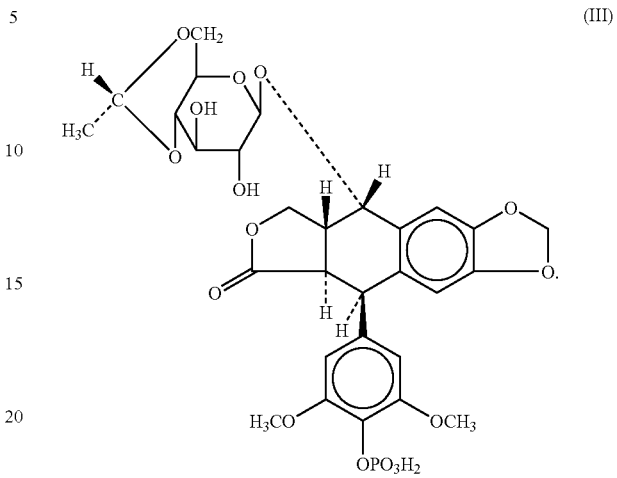

(III)

Compound (IV) can also be referred to as 4'-Demethylepipodophyllotoxin 9-[4,6-O—(R)-ethylidene-β-D-glucopyranoside], 4'-(dihydrogen phosphate) in accordance with IUPAC nomenclature. Use of the term "4'-Demethylepipodophyllotoxin 9-[4,6-O—(R)-ethylidene-β-D-glucopyranoside], 4'-(dihydrogen phosphate)" encompasses (unless otherwise indicated) solvates (including hydrates) and polymorphic forms of the compound (IV) or its salts. Pharmaceutical compositions of 4'-Demethylepipodophyllotoxin 9-[4,6-O—(R)-ethylidene-β-D-glucopyranoside], 4'-(dihydrogen phosphate) and one or more diluents, vehicles and/or excipients. One example of a pharmaceutical composition comprising 4'-Demethylepipodophyllotoxin 9-[4,6-O—(R)-ethylidene-β-D-glucopyranoside], 4'-(dihydrogen phosphate) is ETOPOPHOS (etoposide phosphate). ETOPOPHOS comprises 4'-Demethylepipodophyllotoxin 9-[4,6-O—(R)-ethylidene-β-D-glucopyranoside], 4'-(dihydrogen phosphate) as the active ingredient, for IV infusion including inactive ingredients in a sterile form for intravenous use only, in single-dose vials containing etoposide phosphate equivalent to 100 mg etoposide, 32.7 mg sodium citrate USP, and 300 mg dextran 40.

Suitable anti-proliferative agents for use in the methods of the invention, include, without limitation, taxanes, paclitaxel (paclitaxel is commercially available as TAXOL®), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discodermolide, patupilone (EPO-906), KOS-862, KOS-1584, ZK-EPO, BMS-310705, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14, 16-didemethyl-(+)-discodermolides, and cryptothilone 1, in addition to other microtubuline stabilizing agents known in the art.

The phrase "protein tyrosine kinase inhibitor" is meant to refer to agents that inhibit one or more members of the protein tyrosine kinase family. Non-limiting examples of protein tyrosine kinase inhibitors include, but are not limited to, dasatinib, imatinib, nilotinib, PD180970, GGP76030, AP23464, SKI 606, NS-187, and/or AZD0530. Such protein tyrosine kinase inhibitors may be administered either alone or in combination with other molecules, such as T315I inhibitors.

The phrase "microtubulin modulating agent" is meant to refer to agents that either stabilize microtubulin or destabilize microtubulin synthesis and/or polymerization.

As referenced herein, the at least one anti-proliferative agent may be a microtubule affecting agent. A microtubule affecting agent interferes with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E),7R*,10S*,11R*, 12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in U.S. Pat. No. 6,262,094, issued Jul. 17, 2001), [1S-[1R*,3R*(E),7R*, 10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Ser. No. 09/506,481 filed on Feb. 17, 2000, and examples 7 and 8 herein), and derivatives thereof; and other microtubule-disruptor agents. Additional antineoplastic agents include, discodermolide (see Service, Science, 274: 2009 (1996)) estramustine, nocodazole, MAP4, and the like. Examples of such agents are also described in the scientific and patent literature, see, e.g., Bulinski, J. Cell Sci., 110: 3055-3064 (1997); Panda, Proc. Natl. Acad. Sci. USA, 94:10560-10564 (1997); Muhlradt, Cancer Res., 57:3344-3346 (1997); Nicolaou, Nature, 387:268-272 (1997); Vasquez, Mol. Biol. Cell., 8:973-985 (1997); Panda, J. Biol. Chem., 271:29807-29812 (1996).

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX® can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is CASODEX® which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particularly preferred class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors. The present invention also provides methods for the administration of a protein tyrosine kinase inhibitor, a microtubuline-stabilizing agent, such as paclitaxel; a nucleoside analogue, such as gemcitabine; or a DNA double strand inducing agent, such as etoposide, in synergistic combination(s) with at least one co-stimulatory pathway modulators, particularly an anti-CTLA4 agent, for the treatment and prevention of a proliferative disorder, in addition to a BCR-ABL associated disorder, a mutant BCR-ABL associated disorder, and/or a protein tyrosine kinase-associated disorder, an a disorder associated with the presence of an imatinib-resistant BCR-ABL mutation, a dasatinib-resistant BCR-ABL mutation, CML, imatinib-resistant CML, and/or Imatinib-intolerant CML.

The term "BCR-ABL" as used herein is inclusive of both wild-type and mutant BCR-ABL.

"BCR-ABL associated disorders" are those disorders which result from BCR-ABL activity, including mutant BCR-ABL activity, and/or which are alleviated by the inhibition of BCR-ABL, including mutant BCR-ABL, expression and/or activity. A reciprocal translocation between chromosomes 9 and 22 produces the oncogenic BCR-ABL fusion protein. The phrase "BCR-ABL associated disorders" is inclusive of "mutant BCR-ABL associated disorders".

Disorders included in the scope of the present invention include, for example, leukemias, including, for example, chronic myeloid leukemia, acute lymphoblastic leukemia, and Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia, chronic lymphocytic leukemia, mastocytosis and any symptom associated with mastocytosis. In addition, disorders include urticaria pigmentosa, mastocytosises such as diffuse cutaneous mastocytosis, solitary mastocytoma in human, as well as dog mastocytoma and some rare subtypes like bullous, erythrodermic and teleangiectatic mastocytosis, mastocytosis with an associated hematological disorder, such as a myeloproliferative or myelodysplastic syndrome, or acute leukemia, myeloproliferative disorder associated with mastocytosis, and mast cell leukemia. Various additional cancers are also included within the scope of protein tyrosine kinase-associated disorders including, for example, the following: carcinoma, including that of the bladder, breast, colon, kidney, liver, lung, ovary, pancreas, stomach, cervix, thyroid, testis, particularly testicular seminomas, and skin; including squamous cell carcinoma; gastrointestinal stromal tumors ("GIST"); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer, teratocarcinoma, chemotherapy refractory non-seminomatous germ-cell tumors, and Kaposi's sarcoma. In certain preferred embodiments, the disorder is leukemia, breast cancer, prostate cancer, lung cancer, colon cancer, melanoma, or solid tumors. In certain preferred embodiments, the leukemia is chronic myeloid leukemia (CML), Ph+ ALL, AML, imatinib-resistant CML, imatinib-intolerant CML, accelerated CML, lymphoid blast phase CML.

A "solid tumor" includes, for example, sarcoma, melanoma, carcinoma, prostate carcinoma, lung carcinoma, colon carcinoma, or other solid tumor cancer.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatoma, breast cancer, colon carcinoma, and head and neck cancer, gastric cancer, germ cell tumor, pediatric sarcoma, sinonasal natural killer, multiple myeloma, acute myelogenous leukemia (AML), and chronic lymphocytic leukemia (CML).

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

A "mutant BCR-ABL" encompasses a BCR-ABL tyrosine kinase with an amino acid sequence that differs from wild type BCR-ABL tyrosine kinase by one or more amino acid substitutions, additions or deletions. For example a substitution of the amino acid at position 507 of SEQ ID NO:2 with another amino acid would result in a mutant BCR-ABL tyrosine kinase.

"Mutant BCR-ABL associated disorder" is used to describe a BCR-ABL associated disorder in which the cells involved in said disorder are or become resistant to treatment with a kinase inhibitor used to treat said disorder as a result of a mutation in BCR-ABL. For example, a kinase inhibitor compound can be used to treat a cancerous condition, which compound inhibits the activity of wild type BCR-ABL which will inhibit proliferation and/or induce apoptosis of cancerous cells. Over time, a mutation can be introduced into the gene encoding BCR-ABL kinase, which can alter the amino acid sequence of the BCR-ABL kinase and cause the cancer cells to become resistant, or at least partially resistant, to treatment with the compound. Alternatively, a mutation can already be present within the gene encoding BCR-ABL kinase, either genetically or as a consequence of an oncogenic event, independent of treatment with a protein tyrosine kinase inhibitor, which can be one factor resulting in these cells propensity to differentiate into a cancerous or proliferative state, and also result in these cells being less sensitive to treatment with a protein tyrosine kinase inhibitor. Such situations are expected to result, either directly or indirectly, in a "mutant BCR-ABL kinase associated disorder" and treatment of such condition will require a compound that is at least partially effective against the mutant BCR-ABL, preferably against both wild type BCR-ABL and the mutant BCR-ABL. In the instance where an individual develops at least partial resistance to the kinase inhibitor imatinib, the mutant BCR-ABL associated disorder is one that results from an imatinib-resistant BCR-ABL mutation, or a protein tyrosine kinase inhibitor resistant BCR-ABL mutation. Similarly, in the instance where an individual develops at least partial resistance to the kinase inhibitor N-(2-chloro-6-methylphenyl)-2-[[6-[4-(2-hydroxyethyl)-1-piperazinyl]-2-methyl-4-pyrimidinyl]amino]-5-thiazolecarboxamide, the mutant BCR-ABL associated disorder is one that results from an N-(2-chloro-6-methylphenyl)-2-[[6-[4-(2-hydroxyethyl)-1-piperazinyl]-2-methyl-4-pyrimidinyl]amino]-5- thiazolecarboxamide resistant BCR-ABL mutation, or a protein tyrosine kinase inhibitor resistant BCR-ABL mutation. The present inventors discovered that after treatment with N-(2-chloro-6-methylphenyl)-2-[[6-[4-(2-hydroxyethyl)-1-piperazinyl]-2-methyl-4-pyrimidinyl]amino]-5-thiazolecarboxamide, certain individuals developed E507G mutations. The present invention provides, among other things, methods of treating mutant BCR-ABL associated disorders and methods of identifying if an individual has a mutant BCR-ABL associated disorder.

"Protein tyrosine kinase-associated disorders" of particular interest herein are those disorders which result, at least in part, from aberrant SRC or BCR-ABL (WT or mutant) activity and/or which are alleviated by the inhibition of SRC or BCR-ABL (WT or mutant) referred to herein as "SRC associated disorders", "SRC associated cancer", or "BCR-ABL associated disorders", "BCR-ABL associated cancer"

"Imatinib-resistant BCR-ABL mutation" refers to a specific mutation in the amino acid sequence of BCR-ABL that confers upon cells that express said mutation resistance to treatment with imatinib. As discussed herein such mutations can include mutations at the T315I position of BCR-ABL. Additional mutations that may render a BCR-ABL protein at least partially imatinib resistant can include, for example, E279K, F359I, L364I, L387M, F486S, D233H, T243S, M244V, G249D, G250E, G251S, Q252H, Y253F, Y253H, E255K, E255V, V256L, Y257F, Y257R, F259S, K262E, D263G, K264R, S265R, V268A, V270A, T272A, Y274C, Y274R, D276N, T277P, M278K, E279K, E282G, F283S, A288T, A288V, M290T, K291R, E292G, I293T, P296S, L298M, L298P, V299L, Q300R, G303E, V304A, V304D, C305S, C305Y, T306A, F311L, I314V, T315I, T315A, E316G, F317L, F317I, M318T, Y320C, Y320H, G321E, D325H, Y326C, L327P, R328K, E329V, Q333L, A337V, V339G, L342E, M343V, M343T, A344T, A344V, I347V, A350T, M351T, E352A, E352K, E355G, K357E, N358D, N358S, F359V, F359C, F359I, I360K, I360T, L364H, L364I, E373K, N374D, K378R, V379I, A380T, A380V, D381G, F382L, L387M, M388L, T389S, T392A, T394A, A395G, H396K, H396R, A399G, P402T, T406A, S417Y, F486S, and E507G. Additional Imatinib-resistant BCR-ABL mutations may also include other BCR-ABL mutations disclosed elsewhere herein.

"Dasatinib-resistant BCR-ABL mutation" refers to a specific mutation in the amino acid sequence of BCR-ABL that confers upon cells that express said mutation at least partial resistance to treatment with dasatinib. As discussed herein such mutations can include mutations at the T315I, T315A, F317A, F317I, and E507G position of BCR-ABL. Additional dasatinib-resistant BCR-ABL mutations may also include other BCR-ABL mutations disclosed elsewhere herein.

"Imatinib-resistant CML" refers to a CML in which the cells involved in CML are resistant to treatment with imatinib. Generally it is a result of a mutation in BCR-ABL.

"Imatinib-intolerant CML" refers to a CML in which the individual having the CML is intolerant to treatment with imatinib, i.e., the toxic and/or detrimental side effects of imatinib outweigh any therapeutically beneficial effects.

The synergistic combination of a protein tyrosine kinase inhibitor, microtubuline-stabilizing agent, such as paclitaxel; a nucleoside analogue, such as gemcitabine; or a DNA double strand inducing agent, such as etoposide with a co-stimulatory pathway modulator may also including the addition of one or more additional compounds, which include but are not limited to the following: a tubulin stabilizing agent (e.g., pacitaxol, epothilone, taxane, etc.); a farnysyl transferase inhibitor (e.g., (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt); another protein tyrosine kinase inhibitor; an increased dosing frequency regimen of N-(2-chloro-6-methylphenyl)-2-[[6-[4-(2-hydroxyethyl)-1-piperazinyl]-2-methyl-4-pyrimidinyl]amino]-5-thiazolecarboxamide; the ATP non-competitive inhibitor ONO12380; Aurora kinase inhibitor VX-680; p38 MAP kinase inhibitor BIRB-796; and any other combination or dosing regimen comprising N-(2-chloro-6-methylphenyl)-2-[[6-[4-(2-hydroxyethyl)-1-piperazinyl]-2-methyl-4-pyrimidinyl]amino]-5-thiazolecarboxamide disclosed herein, or any other combination disclosed herein.

A "farnysyl transferase inhibitor" can be any compound or molecule that inhibits farnysyl transferase. The farnysyl transferase inhibitor can have formula (II), (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, hydrochloride salt. The compound of formula (V) is a cytotoxic FT inhibitor which is known to kill non-proliferating cancer cells preferentially. The compound of formula (V) can further be useful in killing stem cells.

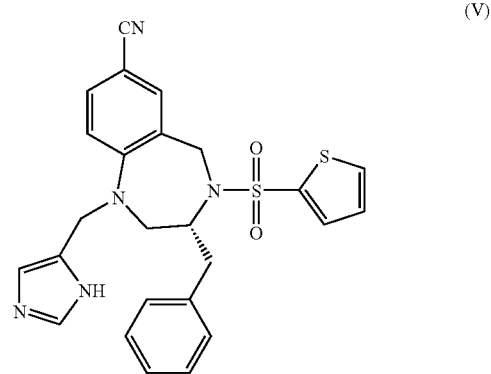

(V)

The compound of formula (V), its preparation, and uses thereof are described in U.S. Pat. No. 6,011,029, which is herein incorporated by reference in its entirety and for all purposes. Uses of the compound of formula (II) are also described in WO 2004/015130, published Feb. 19, 2004, which is herein incorporated by reference in its entirety and for all purposes.

The phrase "protein tyrosine kinase" as used herein includes enzymes that catalyze the transfer of the terminal phosphate of adenosine triphosphate (ATP) to tyrosine residues in protein substrates. Non-limiting examples of tyrosine kinases include receptor tyrosine kinases such as EGFR (e.g., EGFR/HER1/ErbB1, HER2/Neu/ErbB2, HER3/ErbB3, HER4/ErbB4), INSR (insulin receptor), IGF-IR, IGF-II1R, IRR (insulin receptor-related receptor), PDGFR (e.g., PDGFRA, PDGFRB), c-KIT/SCFR, VEGFR-1/FLT-1, VEGFR-2/FLK-1/KDR, VEGFR-3/FLT-4, FLT-3/FLK-2, CSF-1R, FGFR 1-4, CCK4, TRK A-C, MET, RON, EPHA 1-8, EPHB 1-6, AXL, MER, TYRO3, TIE, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106; and non-receptor tyrosine kinases such as BCR-ABL, Src, Frk, Btk, Csk, Abl, Zap70, Fes/Fps, Fak, Jak, Ack, and LIMK. One of skill in the art will know of other receptor and/or non-receptor tyrosine kinases that can be targeted using the inhibitors described herein.

The term "tyrosine kinase inhibitor" includes any of a variety of therapeutic agents or drugs that act as selective or non-selective inhibitors of receptor and/or non-receptor tyrosine kinases. Without being bound to any particular theory, tyrosine kinase inhibitors generally inhibit target tyrosine kinases by binding to the ATP-binding site of the enzyme. Examples of tyrosine kinase inhibitors suitable for use in the methods of the present invention include, but are not limited to, gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima®; ZD6474), nilotinib, derivatives thereof, analogs thereof, and combinations thereof. Additional tyrosine kinase inhibitors suitable for use in the present invention are described in, e.g., U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340. One of skill in the art will know of other tyrosine kinase inhibitors suitable for use in the present invention Methods for the safe and effective administration of most of these chemotherapeutic agents are known to those skilled in the art. In addition, their administration is described in the standard literature.

For example, the administration of many of the chemotherapeutic agents is described in the *Physicians' Desk Reference* (PDR), e.g., 1996 edition (Medical Economics Company, Montvale, N.J. 07645-1742, USA); the disclosure of which is incorporated herein by reference thereto.

The compositions of the present invention may further comprise one or more pharmaceutically acceptable additional ingredient(s) such as alum, stabilizers, antimicrobial agents, buffers, coloring agents, flavoring agents, adjuvants, and the like. The pharmaceutical compositions of the present invention may be administered orally or parenterally including the intravenous, intramuscular, intraperitoneal, subcutaneous, rectal and topical routes of administration.

For oral use, the pharmaceutical compositions of the present invention, may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The co-stimulatory pathway modulator, preferably an anti-CTLA4 agent, described herein may also be delivered transdermally. The transdermal compositions can take the form of creams, lotions, aerosols and/or emulsions and can be included in a transdermal patch of the matrix or reservoir type as are conventional in the art for this purpose.

If formulated as a fixed dose, the active ingredients of the pharmaceutical combination compositions of the present invention are employed within the dosage ranges described below. Alternatively, the co-stimulatory pathway modulator and the protein tyrosine kinase inhibitor may be administered separately in the dosage ranges described below. In a preferred embodiment of the present invention, the co-stimulatory pathway modulator is administered in the dosage range described below following or simultaneously with administration of the protein tyrosine kinase inhibitor in the dosage range described below.

The following sets forth preferred therapeutic combinations and exemplary dosages for use in the methods of the present invention.

| THERAPEUTIC COMBINATION | DOSAGE mg/m² (per dose)[1] |
|---|---|
| First Administration of Dasatinib, with | 50-180 mg BID |
| Administration of anti-CTLA4 Antibody | 0.1-25 mg/kg |
| First Administration of Paclitaxel, with | 40-250 mg/m² |
| Administration of anti-CTLA4 Antibody | 0.1-25 mg/kg |
| First Administration of Gemcitabine with | 200-1250 mg |
| Administration of anti-CTLA4 Antibody | 0.1-25 mg/kg |
| First Administration of Etoposide with | 50-900 mg |
| Administration of anti-CTLA4 Antibody | 0.1-25 mg/kg |

[1]Each combination listed herein optionally includes the administration of an anti-cancer vaccine from about 0.001-100 mg.

While this table provides exemplary dosage ranges of the protein tyrosine kinase inhibitor, preferably SPRYCEL®, a co-stimulator pathway modulator, preferably anti-CTLA4 antibody, and/or anti-cancer vaccine agents, when formulating the pharmaceutical compositions of the invention the clinician may utilize preferred dosages as warranted by the condition of the patient being treated. The anti-CTLA4 antibody may preferably be administered at about 0.3-10 mg/kg, or the maximum tolerated dose. In an embodiment of the invention, a dosage of CTLA-4 antibody is administered about every three weeks. Alternatively, the CTLA-4 antibody may be administered by an escalating dosage regimen including administering a first dosage of CTLA-4 antibody at about 3 mg/kg, a second dosage of CTLA-4 antibody at about 5 mg/kg, and a third dosage of CTLA-4 antibody at about 9 mg/kg.

Likewise, the protein tyrosine kinase inhibitor, preferably SPRYCEL®, may preferably be administered at about 2 times per day at 70 mg. Alternatively, it can be dosed at, for example, about 50, about 70, about 90, about 100, 110, or 120 BID, or 100, 140, or 180 once daily, or the maximum tolerated dose. The dose of a protein tyrosine kinase inhibitor may depend upon a number of factors, including stage of disease, the presence of one or more mutations in the targeted protein tyrosine kinase, BCR-ABL mutations, etc. The specific dose that should be administered based upon the presence of one or more of such factors is within the skill of the artisan.

Likewise, etoposide may preferably be administered at about 50 mg to about 900 mg per day. Etoposide is available for intravenous infusion as a sterile lyophile in single-dose vials containing etoposide phosphate equivalent to 100 mg etoposide, 32.7 mg sodium citrate USP, and 300 mg dextran 40. Alternatively, it can be dosed at, for example, about 50, about 70, about 90, about 100, about 200, about 300, about 400, about 500, about 600, about 700, about 800 or about 900 daily, or the maximum tolerated dose.

Likewise, gemcitabine may preferably be administered at about 200 mg/m to about 1250 mg/m per day by IV over 30 to 90 minute infusion. Gemcitabine is available for intravenous infusion containing from about 200 mg to about 1250 mg of gemcitabine HCl (expressed as free base) formulated with mannitol (200 mg or 1 g, respectively) and sodium acetate (12.5 mg or 62.5 mg, respectively) as a sterile lyophilized powder. Alternatively, it can be dosed at, for example, about 50, about 100, about 200, about 300, about 400, about 500, about 600, about 700, about 800, about 900, about 1000, about 1100, about 1200 or about 1250 daily, or the maximum tolerated dose.

The combinations of the present invention may also be used in conjunction with other well known therapies that are selected for their particular usefulness against the condition that is being treated.

The anti-CTLA4 antibody may preferably be administered at about 0.3-10 mg/kg, or the maximum tolerated dose. In an embodiment of the invention, a dosage of CTLA-4 antibody is administered about every three weeks. Alternatively, the CTLA-4 antibody may be administered by an escalating dosage regimen including administering a first dosage of CTLA-4 antibody at about 3 mg/kg, a second dosage of CTLA-4 antibody at about 5 mg/kg, and a third dosage of CTLA-4 antibody at about 9 mg/kg.

In another specific embodiment, the escalating dosage regimen includes administering a first dosage of CTLA-4 antibody at about 5 mg/kg and a second dosage of CTLA-4 antibody at about 9 mg/kg.

Further, the present invention provides an escalating dosage regimen, which includes administering an increasing dosage of CTLA-4 antibody about every six weeks.

In an aspect of the present invention, a stepwise escalating dosage regimen is provided, which includes administering a first CTLA-4 antibody dosage of about 3 mg/kg, a second CTLA-4 antibody dosage of about 3 mg/kg, a third CTLA-4 antibody dosage of about 5 mg/kg, a fourth CTLA-4 antibody dosage of about 5 mg/kg, and a fifth CTLA-4 antibody dosage of about 9 mg/kg. In another aspect of the present invention, a stepwise escalating dosage regimen is provided, which includes administering a first dosage of 5 mg/kg, a second dosage of 5 mg/kg, and a third dosage of 9 mg/kg.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

When employing the methods or compositions of the present invention, other agents used in the modulation of tumor growth or metastasis in a clinical setting, such as antiemetics, can also be administered as desired.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-CTLA4 agent(s) and protein tyrosine kinase inhibitor) on the patient, and in view of the observed responses of the disease to the administered therapeutic agents.

In the methods of this invention, a protein tyrosine kinase inhibitor, such as dasatinib, a microtubuline-stabilizing agent, such as paclitaxel; a nucleoside analogue, such as gemcitabine; or a DNA double strand inducing agent, such as etoposide is administered simultaneously or sequentially with an anti-CTLA4 agent. Thus, it is not necessary that the anti-CTLA4 therapeutic agent(s) and a microtubuline-stabilizing agent, such as paclitaxel; a nucleoside analogue, such as gemcitabine; or a DNA double strand inducing agent, such as etoposide be administered simultaneously or essentially simultaneously. The advantage of a simultaneous or essentially simultaneous administration is well within the determination of the skilled clinician.

Also, in general, a microtubuline-stabilizing agent, such as paclitaxel; a nucleoside analogue, such as gemcitabine; or a DNA double strand inducing agent, such as etoposide and anti-CTLA4 agent(s) do not have to be administered in the same pharmaceutical composition, and may, because of different physical and chemical characteristics, have to be administered by different routes.

If a microtubuline-stabilizing agent, such as paclitaxel; a nucleoside analogue, such as gemcitabine; or a DNA double strand inducing agent, such as etoposide and the anti-CTLA4 agent(s) are not administered simultaneously or essentially simultaneously, then the initial order of administration of a protein tyrosine kinase inhibitor, such as dasatinib, a microtubuline-stabilizing agent, such as paclitaxel; a nucleoside analogue, such as gemcitabine; or a DNA double strand inducing agent, such as etoposide and the anti-CTLA4 agent(s) may be varied. Thus, for example, a microtubuline-stabilizing agent, such as paclitaxel; a nucleoside analogue, such as gemcitabine; or a DNA double strand inducing agent, such as etoposide may be administered first followed by the administration of the anti-CTLA4 agent(s); or the anti-CTLA4 agent(s) may be administered first followed by the administration of a protein tyrosine kinase inhibitor, a microtubuline-stabilizing agent, such as paclitaxel; a nucleoside analogue, such as gemcitabine; or a DNA double strand inducing agent, such as etoposide. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

Thus, in accordance with experience and knowledge, the practicing physician can modify each protocol for the administration of a component (therapeutic agent—i.e., a protein tyrosine kinase inhibitor, such as dasatinib, a microtubuline-stabilizing agent, such as paclitaxel; a nucleoside analogue, such as gemcitabine; or a DNA double strand inducing agent, such as etoposide, anti-CTLA4 agent(s),) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

As referenced elsewhere herein, the optimal dose for the protein tyrosine kinase inhibitor may depend upon a number of factors, including but limited to the presence of one or more mutations in the targeted protein tyrosine kinase inhibitor and/or in BCR-ABL.

A "therapeutically effective amount" of an inhibitor of a mutant BCR-ABL kinase can be a function of the mutation present. For example Shah et al. disclose that cell lines with certain mutations in BCR-ABL kinase are more sensitive to N-(2-chloro-6-methylphenyl)-2-[[6-[4-(2-hydroxyethyl)-1-piperazinyl]-2-methyl-4-pyrimidinyl]amino]-5-thiazolecarboxamide than cell lines with different BCR-ABL kinase mutations. For example, cells comprising a F317L mutation in BCR-ABL kinase may require three to five-fold higher concentration of N-(2-chloro-6-methylphenyl)-2-[[6-[4-(2-hydroxyethyl)-1-piperazinyl]-2-methyl-4-pyrimidinyl]amino]-5-thiazolecarboxamide than cell lines expressing a F317I mutation. One skilled in the art will appreciate the difference in sensitivity of the mutant BCR-ABL kinase cells and determine a therapeutically effective dose accordingly.

Examples of therapeutically effective doses of N-(2-chloro-6-methylphenyl)-2-[[6-[4-(2-hydroxyethyl)-1-piperazinyl]-2-methyl-4-pyrimidinyl]amino]-5-thiazolecarboxamide that may be warranted based upon the relative sensitivity of BCR-ABL kinase mutants to N-(2-chloro-6-methylphenyl)-2-[[6-[4-(2-hydroxyethyl)-1-piperazinyl]-2-methyl-4-pyrimidinyl]amino]-5-thiazolecarboxamide compared to wild-type BCR-ABL kinase can be determined using various in vitro biochemical assays including cellular proliferation, BCR-ABL tyrosine phosphorylation, peptide substrate phosphorylation, and/or autophosphorylation assays. For example, approximate therapeutically effective doses of N-(2-chloro-6-methylphenyl)-2-[[6-[4-(2-hydroxyethyl)-1-piperazinyl]-2-methyl-4-pyrimidinyl]amino]-5-thiazolecarboxamide can be calculated based upon multiplying the typical dose with the fold change in sensitivity in anyone or more of these assays for each BCR-ABL kinase mutant. O'Hare et al. (*Cancer Res.*, 65(11):4500-4505 (2005), which is hereby incorporated by reference in its entirety and for all purposes) performed analysis of the relative sensitivity of N-(2-chloro-6-methylphenyl)-2-[[6-[4-(2-hydroxyethyl)-1-piperazinyl]-2-methyl-4-pyrimidinyl]amino]-5-thiazolecarboxamide with several clinically relevant BCR-ABL Kinase mutants. For example, the E255V mutant had a fold change of "1" in the GST-Abl kinase assay, whereas this same mutant had a fold change of "14" in the cellular proliferation assay. Thus, a therapeutically relevant dose of N-(2-chloro-6-methylphenyl)-2-[[6-[4-(2-hydroxyethyl)-1-piperazinyl]-2-methyl-4-pyrimidinyl]amino]-5-thiazolecarboxamide for patients harboring this mutation could range, for example, anywhere from 1 to 14 fold higher than the typical dose. Accordingly, therapeutically relevant doses of N-(2-chloro-6-methylphenyl)-2-[[6-[4-(2-hydroxyethyl)-1-piperazinyl]-2-methyl-4-pyrimidinyl]amino]-5-thiazolecarboxamide for any of the BCR-ABL kinase mutants can be, for example, 1, 2, 3, 4, 5, 6, 7, 8, 9, 10, 11, 12, 13, 14, 15, 16, 17, 18, 19, 20, 25, 30, 35, 40, 50, 60, 70, 80, 90, 100, 125, 150, 175, 200, 225, 250, or 300 folder higher than the prescribed dose. Alternatively, therapeutically relevant doses of N-(2-chloro-6-methylphenyl)-2-[[6-[4-(2-hydroxyethyl)-1-piperazinyl]-2-methyl-4-pyrimidinyl]amino]-5-thiazolecarboxamide can be, for example, 0.9×, 0.8×, 0.7×, 0.6×, 0.5×, 0.4×, 0.3×, 0.2×, 0.1×, 0.09×, 0.08×, 0.07×, 0.06×, 0.05×, 0.04×, 0.03×, 0.02×, or 0.01× of the prescribed dose.

According to O'Hare et al., the M244V mutant had a fold change of "1.3" in the GST-Abl kinase assay, a fold change of "1.1" in the autophosphorylation assay, and a fold change of "2" in the cellular proliferation assay; the G250E mutant had a fold change of "0.5" in the GST-Abl kinase assay, a fold change of "3" in the autophosphorylation assay, and a fold change of "2" in the cellular proliferation assay; the Q252H mutant had a fold change of "4" in the cellular proliferation assay; the Y253F mutant had a fold change of "0.6" in the GST-Abl kinase assay, a fold change of "4" in the autophosphorylation assay, and a fold change of "4" in the cellular proliferation assay; the Y253H mutant had a fold change of "3" in the GST-Abl kinase assay, a fold change of "2" in the autophosphorylation assay, and a fold change of "2" in the cellular proliferation assay; the E255K mutant had a fold change of "0.3" in the GST-Abl kinase assay, a fold change of "2" in the autophosphorylation assay, and a fold change of "7" in the cellular proliferation assay; the F317L mutant had a fold change of "1.5" in the GST-Abl kinase assay, a fold change of "1.4" in the autophosphorylation assay, and a fold change of "9" in the cellular proliferation assay; the M351T mutant had a fold change of "0.2" in the GST-Abl kinase assay, a fold change of "2" in the autophosphorylation assay, and a fold change of "1.4" in the cellular proliferation assay; the F359V mutant had a fold change of "0.8" in the GST-Abl kinase assay, a fold change of "2" in the autophosphorylation assay, and a fold change of "3" in the cellular proliferation assay; the H396R mutant had a fold change of "1.3" in the GST-Abl kinase assay, a fold change of "3" in the autophosphorylation assay, and a fold change of "2" in the cellular proliferation assay.

For patients harboring the T315I mutation, either alone or in combination with another BCR-ABL mutation disclosed herein, administration of higher doses of N-(2-chloro-6-methylphenyl)-2-[[6-[4-(2-hydroxyethyl)-1-piperazinyl]-2-methyl-4-pyrimidinyl]amino]-5-thiazolecarboxamide, or combinations of N-(2-chloro-6-methylphenyl)-2-[[6-[4-(2-hydroxyethyl)-1-piperazinyl]-2-methyl-4-pyrimidinyl]amino]-5-thiazolecarboxamide and imatinib; a combination of N-(2-chloro-6-methylphenyl)-2-[[6-[4-(2-hydroxyethyl)-1-piperazinyl]-2-methyl-4-pyrimidinyl]amino]-5-thiazolecarboxamide and a tubulin stabilizing agent (e.g., pacitaxol, epothilone, taxane, etc.); a combination of N-(2-chloro-6- methylphenyl)-2-[[6-[4-(2-hydroxyethyl)-1-piperazinyl]-2-methyl-4-pyrimidinyl]amino]-5-thiazolecarboxamide and a farnysyl transferase inhibitor; a combination of N-(2-chloro-6-methylphenyl)-2-[[6-[4-(2-hydroxyethyl)-1-piperazinyl]-2-methyl-4-pyrimidinyl]amino]-5-thiazolecarboxamide and another protein tyrosine kinase inhibitor; any other combination discloses herein; an increased dosing frequency regimen of N-(2-chloro-6-methylphenyl)-2-[[6-[4-(2-hydroxyethyl)-1-piperazinyl]-2-methyl-4-pyrimidinyl]amino]-5-thiazolecarboxamide; and any other combination or dosing regimen comprising N-(2-chloro-6-methylphenyl)-2-[[6-[4-(2-hydroxyethyl)-1-piperazinyl]-2-methyl-4-pyrimidinyl]amino]-5-thiazolecarboxamide disclosed herein, may be warranted. Alternatively, combinations of N-(2-chloro-6-methylphenyl)-2-[[6-[4-(2-hydroxyethyl)-1-piperazinyl]-2-methyl-4-pyrimidinyl]amino]-5-thiazolecarboxamide with a T315I inhibitor may also be warranted.

Dosage regimens involving N-(2-chloro-6-methylphenyl)-2-[[6-[4-(2-hydroxyethyl)-1-piperazinyl]-2-methyl-4-pyrimidinyl]amino]-5-thiazolecarboxamide useful in practicing the present invention are described in U.S. Ser. No. 10/395,503, filed Mar. 24, 2003; and *Blood* (ASH Annual Meeting Abstracts) 2004, Volume 104: Abstract 20, "Hematologic and Cytogenetic Responses in imatinib-Resistant Accelerated and Blast Phase Chronic Myeloid Leukemia (CML) Patients Treated with the Dual SRC/ABL Kinase Inhibitor N-(2-chloro-6-methylphenyl)-2-[[6-[4-(2-hydroxyethyl)-1-piperazinyl]-2-methyl-4-pyrimidinyl]amino]-5-thiazolecarboxamide: Results from a Phase I Dose Escalation Study", by Moshe Talpaz, et al.; which are hereby incorporated herein by reference in their entirety and for all purposes.

Additional Anti-CTLA4 Compositions

The present invention also encompasses additional anti-CTLA-4 agents including, but not limited to, an anti-CTLA-4 antibody, an anti-CTLA-4 adnectin, an anti-CTLA-4 RNAi, single chain anti-CTLA-4 antibody fragments, domain anti-CTLA-4 antibody fragments, and an anti-CTLA-4 antisense molecule.

A preferred anti-CTLA4 agent of the present invention is the anti-CTLA4 antibody ipilimumab. Other anti-CTLA4 antibodies and fragments are encompassed by the present invention which immunospecifically bind a polypeptide, polypeptide fragment, or variant of CTLA4, and/or an epitope of CTLA4 (as determined by immunoassays well known in the art for assaying specific antibody-antigen binding). Antibodies include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')$_2$ fragments) which are capable of specifically binding to protein. Fab and F(ab')$_2$ fragments lack the Fc fragment of intact antibody, clear more rapidly from the circulation of the animal or plant, and may have less non-specific tissue binding than an intact antibody (Wahl et al., *J. Nucl. Med.*, 24:316-325 (1983)). Thus, these fragments are preferred, as well as the products of a FAB or other immunoglobulin expression library. Moreover, anti-CTLA4 antibodies include chimeric, single chain, and humanized antibodies.

The anti-CTLA4 antibodies can be produced by any method known in the art for the synthesis of antibodies, in particular, by chemical synthesis or preferably, by recombinant expression techniques.

The adnectins of the present invention may be made according to the methods outlined in co-owned U.S. published patent applications Nos. US 2007/0082365, and US 2008/0139791.

Techniques described for the production of single chain antibodies (U.S. Pat. No. 4,946,778; Bird, *Science*, 242:423-442 (1988); Huston et al., *Proc. Natl. Acad. Sci. USA*, 85:5879-5883 (1988); and Ward et al., *Nature*, 334:544-554 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science*, 242:1038-1041 (1988)).

Recombinant expression of an anti-CTLA4 antibody, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an anti-CTLA4 antibody molecule or a heavy or light chain of an antibody, or portion thereof (preferably containing the heavy or light chain variable domain), has been obtained, the vector for the production of the anti-CTLA4 antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an anti-CTLA4 antibody, or a heavy or light chain thereof, or a heavy or light chain variable domain, operably linked to a promoter. Such vectors may include the nucleotide sequence encoding the constant region of the antibody molecule (see, e.g., PCT Publication Nos. WO 86/05807 and WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an anti-CTLA4 antibody. Thus, the invention includes host cells containing a polynucleotide encoding an anti-CTLA4 antibody, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the anti-CTLA4 antibody molecules. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101 (1986); Cockett et al., *Bio/Technology*, 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.*, 2:1791 (1983)), in which the antibody coding sequence may be ligated individually into the vector in frame with the lac Z coding region so that a fusion protein is produced; pIN vectors (Inouye et al., *Nucleic Acids Res.*, 13:3101-3109 (1985); Van Heeke et al., *J. Biol. Chem.*, 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the anti-CTLA4 antibody coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan et al., *Proc. Natl. Acad. Sci. USA*, 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., *Meth. Enzymol.*, 153:516-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the anti-CTLA4 antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the anti-CTLA4 antibody molecule.

A number of selection systems may be used, including but not limited to the herpes simplex virus thymidine kinase (Wigler et al., *Cell*, 11:223 (1977)), hypoxanthine-guanine phosphoribosyltransferase (Szybalska et al., *Proc. Natl. Acad. Sci. USA*, 48:202 (1992)), and adenine phosphoribosyltransferase (Lowy et al., *Cell*, 22:817 (1980)) genes can be employed in tk–, hgprt– or aprt– cells, respectively. Also, antimetabolite resistance can be used as the basis of selection for the following genes: dhfr, which confers resistance to methotrexate (Wigler et al., *Proc. Natl. Acad. Sci. USA*, 77:357 (1980); O'Hare et al., *Proc. Natl. Acad. Sci. USA*, 78:1527 (1981)); gpt, which confers resistance to mycophenolic acid (Mulligan et al., *Proc. Natl. Acad. Sci. USA,* 78:2072 (1981)); neo, which confers resistance to the aminoglycoside G-418 *Clinical Pharmacy,* 12(7):488-505 (1993); Wu et al., *Biotherapy,* 3:87-95 (1991); Tolstoshev, *Ann. Rev. Pharmacol. Toxicol.,* 32:573-596 (1993); Mulligan, *Science,* 260:926-932 (1993); and Morgan et al., *Ann. Rev. Biochem.,* 62:191-217 (1993); *TIB TECH,* 11(5):155-215 (May 1993)); and hygro, which confers resistance to hygromycin (Santerre et al., *Gene,* 30:147 (1984)). Methods commonly known in the art of recombinant DNA technology may be routinely applied to select the desired recombinant clone, and such methods are described, for example, in Ausubel et al., eds., *Current Protocols in Molecular Biology,* John Wiley & Sons, NY (1993); Kriegler, *Gene Transfer and Expression, A Laboratory Manual,* Stockton Press, NY (1990); and in Chapters 12 and 13, Dracopoli et al., eds., *Current Protocols in Human Genetics,* John Wiley & Sons, NY (1994); Colberre-Garapin et al., *J. Mol. Biol.,* 150:1 (1981), which are incorporated by reference herein in their entireties.

The expression levels of an anti-CTLA4 antibody molecule can be increased by vector amplification (for a review, see Bebbington et al., "The use of vectors based on gene amplification for the expression of cloned genes in mammalian cells" in *DNA Cloning,* Vol. 3, Academic Press, NY (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.,* 3:257 (1983)).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature,* 322:52 (1986); Kohler, *Proc. Natl. Acad. Sci. USA,* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the anti-CTLA4 antibodies or fragments thereof can be fused to heterologous polypeptide sequences described herein or otherwise known in the art, to facilitate purification.

The present invention further includes compositions comprising polypeptides or conjugated to anti-CTLA4 antibody domains other than the variable regions. For example, the polypeptides may be fused or conjugated to an antibody Fc region, or portion thereof. The anti-CTLA4 antibody portion fused to a polypeptide may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603, 5,622,929, 5,359,046, 5,349,053, 5,447,851, and 5,112,946; EP 307,434; EP 367,166; PCT Publication Nos. WO 96/04388 and WO 91/06570; Ashkenazi et al., *Proc. Natl. Acad. Sci. USA,* 88:10535-10539 (1991); Zheng et al., *J. Immunol.,* 154:5590-5600 (1995); and Vil et al., *Proc. Natl. Acad. Sci. USA,* 89:11337-11341 (1992) (said references incorporated by reference in their entireties).

Further, an anti-CTLA4 antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See PCT Publication No. WO 97/33899), AIM II (See PCT Publication No. WO 97/34911), Fas Ligand (Takahashi et al., *Int. Immunol.,* 6:1567-1574 (1994)), VEGI (See PCT Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies for Immunotargeting of Drugs in Cancer Therapy", in *Monoclonal Antibodies and Cancer Therapy,* Reisfeld et al., eds., pp. 243-256, Alan R. Liss, Inc. (1985); Hellstrom et al., "Antibodies for Drug Delivery", in *Controlled Drug Delivery,* 2nd Ed., Robinson et al., eds., pp. 623-653, Marcel Dekker, Inc. (1987); Thorpe, "Antibody Carriers of Cytotoxic Agents in Cancer Therapy: A Review", in *Monoclonal Antibodies '84: Biological and Clinical Applications,* Pinchera et al., eds., pp. 475-506 (1985); "Analysis, Results, and Future Prospective of the Therapeutic Use of Radiolabeled Antibody in Cancer Therapy", in *Monoclonal Antibodies for Cancer Detection and Therapy*, Baldwin et al., eds., pp. 303-316, Academic Press (1985), and Thorpe et al., "The Preparation and Cytotoxic Properties of Antibody-Toxin Conjugates", *Immunol. Rev.*, 62:119-158 (1982).

Alternatively, an anti-CTLA4 antibody can be conjugated to a second antibody to form an antibody heteroconjugate as described by Segal in U.S. Pat. No. 4,676,980, which is incorporated herein by reference in its entirety.

An anti-CTLA4 antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., *Medicina* (Aires), 59(6): 753-758, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

A number of methods may be employed to create MIPs to a specific receptor, ligand, polypeptide, peptide, organic molecule. Several preferred methods are described by Esteban et al. in *J. Anal., Chem.*, 370(7):795-802 (2001), which is hereby incorporated herein by reference in its entirety in addition to any references cited therein. Additional methods are known in the art and are encompassed by the present invention, such as for example, Hart, B. R. et al., *J. Am. Chem., Soc.*, 123(9): 2072-2073 (2001); and Quaglia, M. et al., *J. Am. Chem., Soc.*, 123(10):2146-2154 (2001); which are hereby incorporated by reference in their entirety herein.

Antisense oligonucleotides may be single or double stranded. Double stranded RNA's may be designed based upon the teachings of Paddison et al., *Proc. Nat. Acad. Sci.*, 99:1443-1448 (2002); and PCT Publication Nos. WO 01/29058, and WO 99/32619; which are hereby incorporated herein by reference.

Double stranded RNA may also take the form of an RNA inhibitor ("RNAi") such that they are competent for RNA interference. For example, anti-CTLA4 RNAi molecules may take the form of the molecules described by Mello and Fire in PCT Publication Nos. WO 1999/032619 and WO 2001/ 029058; U.S. Publication Nos. 2003/0051263, 2003/ 0055020, 2003/0056235, 2004/265839, 2005/0100913, 2006/0024798, 2008/0050342, 2008/0081373, 2008/ 0248576, and 2008/055443; and/or U.S. Pat. Nos. 6,506,559, 7,282,564, 7,538,095, and 7,560,438. The teachings of these patent and patent applications are hereby incorporated herein by reference in their entirety.

For example, the anti-CTLA4 RNAi molecules may be double stranded RNA, and between about 25 to 400 nucleotides in length, and complementary to the encoding nucleotide sequence of CTLA4. Such RNAi molecules may be about 20, about 25, about 30, about 35, about 45, and about 50 nucleotides in length. In this context, the term "about" is construed to be about 1, 2, 3, 4, 5, or 6 nucleotides longer in either the 5' or 3' direction, or both.

Alternatively, the anti-CTLA4 RNAi molecules of the present invention may take the form be double stranded RNAi molecules described by Kreutzer in European Patent Nos. EP 1144639, and EP 1214945. The teachings of these patent and patent applications are hereby incorporated herein by reference in their entirety. Specifically, the anti-CTLA4 RNAi molecules of the present invention may be double stranded RNA that is complementary to the coding region of CTLA4, and is between about 15 to about 49 nucleotides in length, and preferably between about 15 to about 21 nucleotides in length. In this context, the term "about" is construed to be about 1, 2, 3, 4, 5, 6, 7, 8, 9, or 10 nucleotides longer in either the 5' or 3' direction, or both. Such anti-CTLA-4 molecules can be stabilized by chemical linkage of the single RNA strands.

Alternatively, the anti-CTLA4 RNAi molecules of the present invention may take the form be double stranded RNAi molecules described by Tuschl in European Patent No. EP 1309726. The teachings of these patent and patent applications are hereby incorporated herein by reference in their entirety. Specifically, the anti-CTLA4 RNAi molecules of the present invention may be double stranded RNA that is complementary to the coding region of CTLA4, and is between about 21 to about 23 nucleotides in length, and are either blunt ended or contain either one or more overhangs on the 5' end or 3' end of one or both of the strands with each overhang being about 1, 2, 3, 4, 5, 6, or more nucleotides in length. The ends of each strand may be modified by phosphorylation, hydroxylation, or other modifications. In addition, the internucleotide linkages of one or more of the nucleotides may be modified, and may contain 2'-OH. In this context, the term "about" is construed to be about 1, 2, 3, 4, 5, 6, 7, 8, 9, or 10 nucleotides longer in either the 5' or 3' direction, or both. Such anti-CTLA-4 molecules can be stabilized by chemical linkage of the single RNA strands.

Alternatively, the anti-CTLA4 RNAi molecules of the present invention may take the form be double stranded RNAi molecules described by Tuschl in U.S. Pat. Nos. 7,056,704 and 7,078,196. The teachings of these patent and patent applications are hereby incorporated herein by reference in their entirety. Specifically, the anti-CTLA4 RNAi molecules of the present invention may be double stranded RNA that is complementary to the coding region of CTLA4, and is between about 19 to about 25 nucleotides in length, and are either blunt ended or contain either one or more overhangs on the 5' end or 3' end of one or both of the strands with each overhang being about 1, 2, 3, 4, or 5 or more nucleotides in length. The ends of each strand may be modified by phosphorylation, hydroxylation, or other modifications. In addition, the internucleotide linkages of one or more of the nucleotides may be modified, and may contain 2'-OH. In this context, the term "about" is construed to be about 1, 2, 3, 4, 5, 6, 7, 8, 9, or 10 nucleotides longer in either the 5' or 3' direction, or both.

Such anti-CTLA-4 molecules can be stabilized by chemical linkage of the single RNA strands.

Additionally, the anti-CTLA4 RNAi molecules of the present invention may take the form be RNA molecules described by Crooke in U.S. Pat. Nos. 5,898,031, 6,107,094, 7,432,249, and 7,432,250, and European Application No. EP 0928290. The teachings of these patent and patent applications are hereby incorporated herein by reference in their entirety. Specifically, the anti-CTLA4 molecules may be single stranded RNA, containing a first segment having at least one ribofuranosyl nucleoside subunit which is modified to improve the binding affinity of said compound to the preselected RNA target when compared to the binding affinity of an unmodified oligoribonucleotide to the RNA target; and a second segment comprising at least four consecutive ribofuranosyl nucleoside subunits having 2'-hydroxyl moieties thereon; said nucleoside subunits of said oligomeric compound being connected by internucleoside linkages which are modified to stabilize said linkages from degradation as compared to phosphodiester linkages. Preferably, such RNA molecules are about 15 to 25 nucleotides in length, or about 17 to about 20 nucleotides in length. Preferably such molecules are competent to activate a double-stranded RNAse enzyme to effect cleavage of CTLA4 RNA. In this context, the term "about" is construed to be about 1, 2, 3, 4, 5, 6, 7, 8, 9, or 10 nucleotides longer in either the 5' or 3' direction, or both. Such anti-CTLA-4 molecules can be stabilized by chemical linkage of the single RNA strands.

SiRNA reagents are specifically contemplated by the present invention. Such reagents are useful for inhibiting expression of the polynucleotides of the present invention and may have therapeutic efficacy. Several methods are known in the art for the therapeutic treatment of disorders by the administration of siRNA reagents. One such method is described by Tiscornia et al. (*Proc. Natl. Acad. Sci.,* 100(4):1844-1848 (2003)); WO 04/09769, filed Jul. 18, 2003; and Reich, S. J. et al., *Mol. Vis.,* 9:210-216 (May 30, 2003), which are incorporated by reference herein in its entirety.

In order to facilitate a further understanding of the invention, the following examples are presented primarily for the purpose of illustrating more specific details thereof. The scope of the invention should not be deemed limited by the examples, but to encompass the entire subject matter defined by the Claims.

EXAMPLES

Example 1

Method of Assessing the Effect of the Combination of a Protein Tyrosine Kinase Inhibitor with a Co-Stimulatory Pathway Modulator on Tumor Growth in Three Murine Tumor Models The effect of dasatinib on immune function has been the subject of recent investigations. Some reports demonstrated that in vitro, dasatinib (concentrations of 10-50 nM), inhibits T-cell function, as measured by inhibition of cytokine secretion and degranulation (Weischel et al., 2008) which was postulated to be the result of Lck inhibition. Other reports demonstrated that dasatinib produced blockade of T-cell activation (Schade et al., 2007). However, treatment with dasatinib might also have immunomodulatory effects based on its potent inhibition of STAT3, which may result in maturation of dendritic cells and modulation of T-cell responses (Yu H. et al., 2007), and the differential sensitivity of T effectors and T regulatory cells to inhibition of T-cell signaling (Siggs et al., 2007). Furthermore, large granular lymphocytes have been detected in pleural effusions from patients treated with dasatinib, and of interest, all of these patients had at least one HLA-A2 allele (Mustojski et al., 2008). It is hypothesized that LGL infiltration might be the result of immunostimulation. Thus, there was an interest in determining whether a potentiation of an antitumor immune response could be achieved by the combination of a CTLA-4 blocking mAb and dasatinib in models where dasatinib had minimal effect.

Efficacy studies were conducted in 3 models: SA1N fibrosarcoma, CT26 colon carcinoma and M109 lung carcinoma. The first 2 models are sensitive to the effect of CTLA-4 blockade, whereas dasatinib showed modest antitumor activity in the SA1N model but minimal activity against the CT 26 and M109 models. As shown in FIG. 1A-1B and FIG. 2 concurrent treatment with CTLA-4 mAb+dasatinib resulted in synergistic effects. Synergy was observed when dasatinib was administered at 30 mg/kg either on a daily dosing regimen or following an intermittent schedule (5 days on/2 days off). No synergy was seen in the M109 tumor model.

Figure 3B:
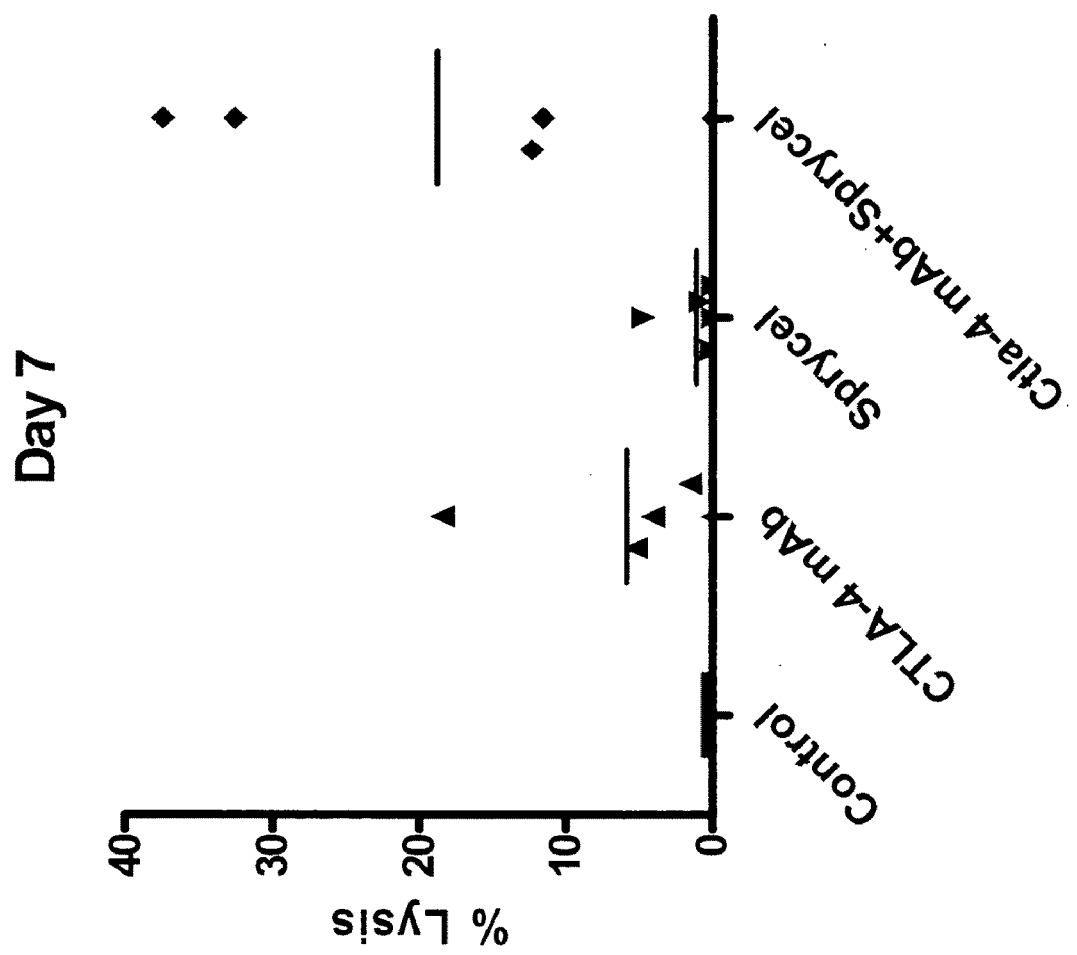
Figure 3C:
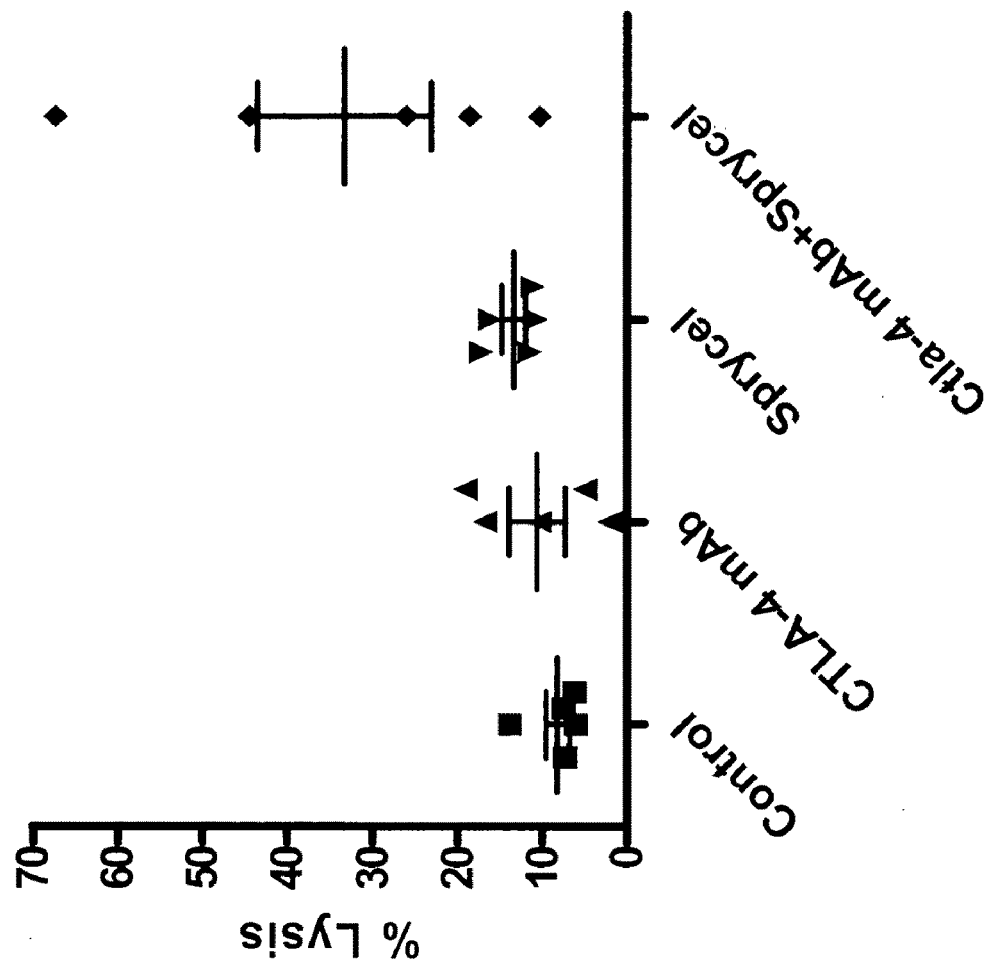
Figure 4B:
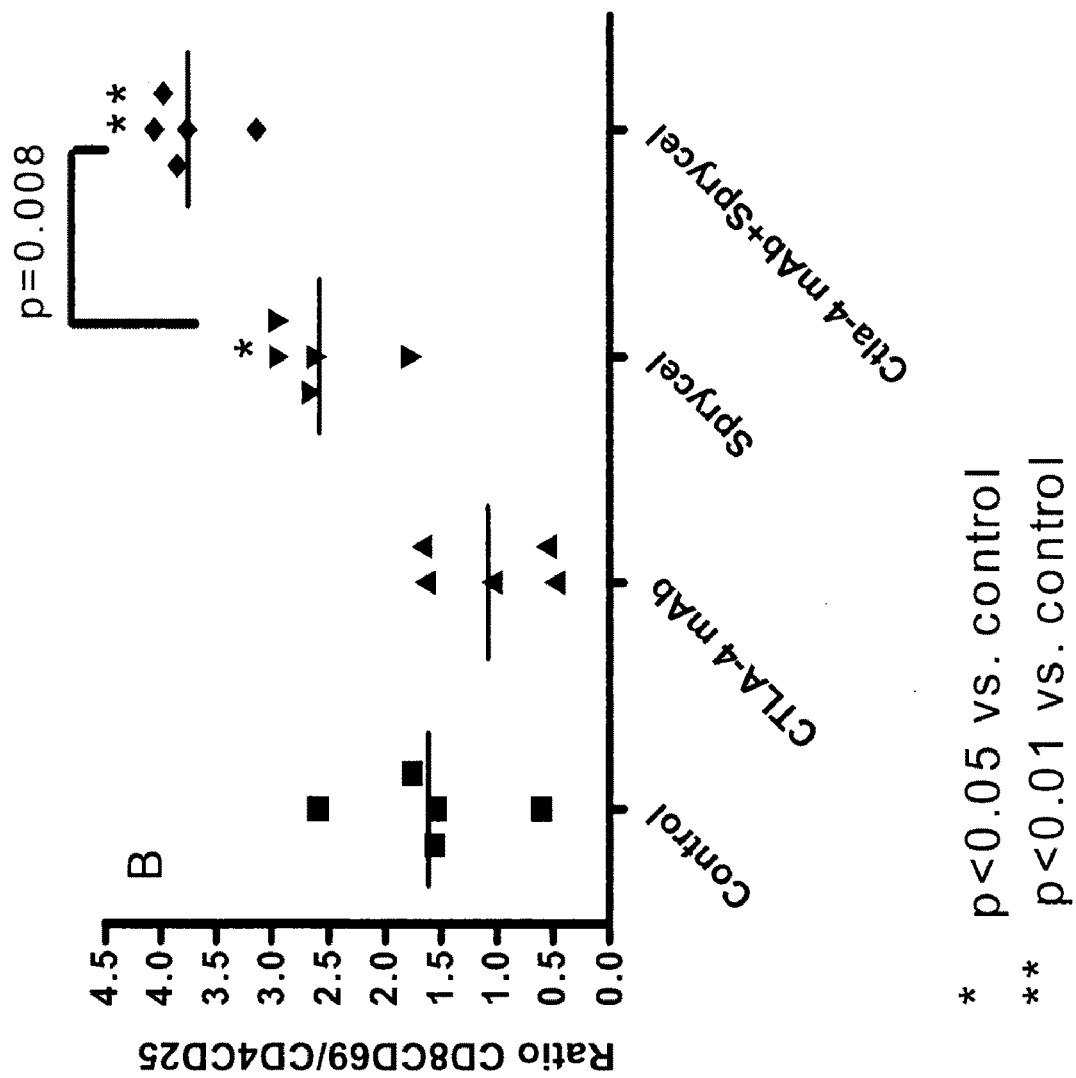

Additional studies were conducted in the CT26 tumor model to determine whether the effect of the combination was due to an expansion of cytotoxic T cells and to determine whether the treatments were altering the composition of the immune cells in the tumor-draining lymph nodes. Increased cytolytic activity was observed in animals treated with the combination treatment compared to animals treated with single treatments (FIG. 3A-3C). Additionally, when the ratio of T effector cells/T regulatory cells (suppressor population) was measured, the combination treatment and the dasatinib-treated group showed an enhanced ratio, indicating a higher number of T effector cells over T regulatory cells. Based on the results obtained in the CT-26 model it is likely that addition of dasatinib to CTLA-4 therapy reduces the number of T regulatory cells while expanding the percentage of T effector cells resulting in an enhancement of the antitumor immune response elicited by anti-CTLA-4 monotherapy.

Example 2

Method of Assessing the Effect of the Combination of a Protein Tyrosine Kinase Inhibitor with a Co-Stimulatory Pathway Modulator on Tumor Growth in a P815 Mastocytoma Murine Tumor Model Concurrent treatment with SPRYCEL® and CTLA-4 antibody was assessed in a P815 mastocytoma murine tumor model. The methods utilized were essentially as outlined in Example 1 herein.

SPRYCEL® showed modest antitumor activity in the P815 model. As shown in FIG. 5, concurrent treatment with CTLA-4 mAb+SPRYCEL® resulted in synergistic effects. Synergy was observed when SPRYCEL® was administered at 30 mg/kg either on a daily dosing regimen or following an intermittent schedule (5 days on/2 days off).

These results were consistent with the results observed in the SA1N and CT26 tumor models (see FIGS. 1A-B and 2), and confirms the administration of a protein tyrosine kinase inhibitor in combination with a CTLA-4 antibody results in synergistic reduction in tumor proliferation.

Example 3

Method of Assessing the Antitumor Activity of Cytotoxic T-Lymphocyte Antigen-4 (CTLA-4) Blockade Alone or Combined with Paclitaxel (Pac), Etoposide (Eto), or Gemcitabine (Gem) In Murine Models To determine if the antitumor activity of an anti-CTLA-4 monoclonal antibody (CTLA-4 mAb) is synergized or inhibited by the addition of chemotherapeutic agents, CTLA-4 mAb was evaluated alone and in combination with Pac, Eto, or Gem in murine tumor models. M109 lung carcinoma, SA1N fibrosarcoma, and CT26 colon carcinoma models were chosen based on different sensitivity to the chemotherapeutic agents and CTLA-4 blockade.

All compounds were tested at their optimal dose and schedule. When used in combination, CTLA-4 mAb was initiated one day after the first dose of chemotherapy. Percent tumor growth inhibition and number of days to reach target tumor size were used to evaluate efficacy. Antitumor activity was scored as: complete regression (CR; non-palpable tumor for $\geq 2$ assessments) or partial regression (PR; 50% reduction in tumor volume for $\geq 2$ assessments). Synergy was defined as antitumor activity significantly superior (p<0.05) to the activity of monotherapy with each agent.

In the M109 subcutaneous tumor model, which is insensitive to CTLA-4 blockade and modestly sensitive to Pac, Eto, and Gem, borderline synergy was evident with the combination of CTLA-4 mAb and Pac, whereas no effect was observed with Eto. Gem monotherapy did not produce significant M109 antitumor activity; however, combining Gem with CTLA-4 mAb resulted in synergy. In the M109 lung metastasis model, synergy was detected for CTLA-4 mAb combined with Eto, borderline synergy was found with Gem, and Pac did not enhance activity.

SA1N fibrosarcoma is sensitive to CTLA-4 blockade and all three chemotherapies. Pac, Eto, and Gem enhanced the activity of CTLA-4 mAb in this model, but synergy was only observed with Eto. CTLA-4 mAb and Pac were ineffective against established CT26 colon carcinoma tumors, but synergistic when the tumor burden was minimal. Both Eto and Gem were effective as single agents in this model and the activity of both was significantly synergized by CTLA-4 mAb.

In summary, addition of CTLA-4 mAb to Eto, Gem, or Pac resulted in model-dependent synergistic activities. Synergy was observed regardless of the immunogenicity of the tumor and only when at least one of the therapies was active. All combination regimens were well-tolerated and the chemotherapies did not appear to inhibit CTLA-4 mAb activity in the SA1N tumor model. Of particular importance, synergy was observed in tumors unresponsive to CTLA-4 mAb alone, suggesting that the chemotherapeutic agents might have induced immunogenic cell death. These findings provide support for the evaluation of chemoimmunotherapy combinations in clinical trials. Data for combinations in each murine model are outlined individually in the following examples.

Example 4

Method of Assessing the Antitumor Activity of

Cytotoxic T-Lymphocyte Antigen-4 (CTLA-4) Blockade Alone or Combined with Paclitaxel (Pac), Etoposide (Eto), or Gemcitabine (Gem) in a Subcutaneous M109 Murine Tumor Model The affect of Paclitaxel, Etoposide and Gemcitabine in combination with CTLA-4 blockage was assessed in a subcutaneous M109 lung carcinoma tumor model to establish the efficacy of each treatment combination.

M109 tumors are insensitive to CTLA-4 blockade and modestly sensitive to Paclitaxel, Etoposide and Gemcitabine. Combination of CTLA-4+Paclitaxel produced enhanced antitumor activity compared to each agent alone, while no enhancement was seen with Etoposide. On the other hand, even though Gemcitabine as single agent did not produce significant antitumor activity, Gemcitabine plus CTLA-4 mAb produced synergistic effects (Table 1).

TABLE 1

Antitumor Activity of CTLA-4 mAb in Combination with Paclitaxel, Etoposide and Gemcitabine in the M109 Lung Carcinoma Subcutaneous Tumor Model

| Treatment | Dose (mg/kg) | Schedule (Study Days) | % TGI (Average) | T-C (1000 mm$^3$) | PR | CR | Outcome |
|---|---|---|---|---|---|---|---|
| CTLA-4 mAb (clone UC10) | 20 | 8, 12, 16 | 0 | 0 | 0 | 0 | |
| Paclitaxel | 24 | 7, 11, 15 | 45 | 5 | 0 | 0 | |
| Paclitaxel + CTLA-4 mAb | 24 20 | 7, 11, 15 8, 12, 16 | 62 | 8 | 0 | 0 | Borderline synergy |
| Etoposide | 50 | 7, 14, 21 | 59 | 9 | 0 | 0 | |
| Etoposide + CTLA-4 mAb | 50 20 | 7, 14, 21 8, 12, 16 | 65 | 11 | 0 | 0 | |
| Gemcitabine | 120 | 7, 11, 15 | 32 | 2.2 | 0 | 0 | |
| Gemcitabine + CTLA-4 mAb | 120 20 | 14, 18, 22 8, 12, 16 | 62 | 11 | 0 | 0 | Synergy |

TVDT = 5.4 days

Example 5

Method of Assessing the Antitumor Activity of Cytotoxic T-Lymphocyte Antigen-4 (CTLA-4) Blockade Alone or Combined with Paclitaxel (Pac), Etoposide (Eto), or Gemcitabine (Gem) in an Experimental Lung Metastatis M109 Murine Tumor Model The affect of Paclitaxel, Etoposide and Gemcitabine in combination with CTLA-4 blockage was assessed in an experimental M109 lung metastasis tumor model to establish the efficacy of each treatment combination.

In the M019 lung metastasis model, Etoposide and CTLA-4 mAb showed synergistic activity while combination with Gemcitabine was borderline synergistic (Table 2).

TABLE 2

Effect of CTLA-4 mAb in combination with chemotherapeutic agents in the M019 lung carcinoma model of experimental pulmonary metastasis

| | Dose (mg/kg) | Schedule (Study Days) | Median Survival Time (days) | Combination Effect |
|---|---|---|---|---|
| Control vehicle | | | 32 | |
| CTLA-4 mAb | 20 | 5, 9, 13 | 33 | |
| Gemcitabine | 150 | 4, 8, 12 | 42 | |
| Gemcitabine + CTLA-4 mAb | 150 / 20 | 4, 8, 12 / 5, 9, 13 | 47 | Borderline synergy |
| Etoposide | 50 | 4, 11, 18 | 34 | |
| Etoposide + CTLA-4 mAb | 50 / 20 | 4, 11, 18 / 5, 9, 13 | 43 | Synergy |
| Paclitaxel | 24 | 4, 8, 12 | 38 | |
| Paclitaxel + CTLA-4 mAb | 24 / 20 | 4, 8, 12 / 5, 9, 13 | 39 | |

Example 6

Method of Assessing the Antitumor Activity of Cytotoxic T-Lymphocyte Antigen-4 (CTLA-4) Blockade Alone or Combined with Paclitaxel (Pac), Etoposide (Eto), or Gemcitabine (Gem) in an SA1N Fibrosarcoma Subcutaneous Murine Tumor Model The affect of Paclitaxel, Etoposide and Gemcitabine in combination with CTLA-4 blockage was assessed in an SA1N fibrosarcoma subcutaneous murine tumor model to establish the efficacy of each treatment combination.

SA1N is an immunogenic tumor line sensitive to CTLA-4 mAb and chemotherapy. While the 3 chemotherapeutic agents tested enhanced the activity of CTLA-4 mAb, synergy was only observed with Etoposide (Table 3).

TABLE 3

Antitumor Activity of CTLA-4 mAb in Combination with Paclitaxel, Etoposide and Gemcitabine in the SA1N Fibrosarcoma Subcutaneous Tumor Model

| Treatment | Dose (mg/kg) | Schedule (Study Days) | % TGI (Average D 20-48) | T-C (1000 mm³) | PR | CR | Outcome |
|---|---|---|---|---|---|---|---|
| CTLA-4 mAb (clone UC10) | 10 | 15, 19, 23 | 81 | 23 | 1/8 | 1/8 | |
| Paclitaxel | 24 | 14, 18, 22 | 65 | 13 | 0/8 | 0/8 | |
| Paclitaxel + CTLA-4 mAb | 24 / 10 | 14, 18, 22 / 15, 19, 23 | 97 | 29 | 2/8 | 1/8 | |
| Etoposide | 40 | 14, 21, 28 | 88 | 14 | 1/8 | 0/8 | |
| Etoposide + CTLA-4 mAb | 40 / 10 | 14, 21, 28 / 15, 19, 23 | 112 | >50 | 2/7 | 5/7 | Synergy |
| Gemcitabine | 120 | 14, 18, 22 | 68 | 11 | 0/8 | 0/8 | |
| Gemcitabine + CTLA-4 mAb | 120 / 10 | 14, 18, 22 / 15, 19, 23 | 94 | 23 | 0/7 | 2/7 | |

TVDT = 8.2 (1000 mm3)

Example 7

Method of Assessing the Antitumor Activity of Cytotoxic T-Lymphocyte Antigen-4 (CTLA-4) Blockade Alone or Combined with Paclitaxel (Pac), Etoposide (Eto), or Gemcitabine (Gem) in a CT26 Colon Carcinoma Murine Tumor Model The affect of Paclitaxel, Etoposide and Gemcitabine in combination with CTLA-4 blockage was assessed in an CT26 colon carcinoma murine tumor model to establish the efficacy of each treatment combination.

CTLA-4 and Paclitaxel are ineffective therapies against CT26 colon carcinoma tumors; their combination was ineffective against established tumors, but synergistic against minimal tumor burden. As shown in Table 4, both Etoposide and Gemcitabine were effective as single agents, but their activity was significantly potentiated by the addition of CTL-4 mAb.

TABLE 4

Antitumor Activity of CTLA-4 mAb in Combination with Paclitaxel, Etoposide and Gemcitabine in the CT26 Colon carcinoma Subcutaneous Tumor Model

| Treatment | Dose (mg/kg) | Schedule (Study Days) | % TGI (Average) | T-C (1000 mm$^3$) | PR | CR | Outcome |
|---|---|---|---|---|---|---|---|
| CTLA-4 mAb (clone UC10) | 20 | 9, 13, 17 | 5 | 0 | 0/8 | 0/8 | |
| Paclitaxel | 24 | 8, 12, 16 | 0 | 0 | 0/8 | 0/8 | |
| Paclitaxel + CTLA-4 mAb | 24 20 | 8, 12, 16 9, 13, 17 | 0 | 1 | 0/8 | 1/8 | |
| Etoposide | 50 | 8, 15, 22 | 66 | 11 | 0/8 | 1/8 | |
| Etoposide + CTLA-4 mAb | 50 20 | 8, 15, 22 9, 13, 17 | 91 | >50 | 1/8 | 4/8 | Synergy |
| Gemcitabine | 120 | 8, 12, 16 | 102 | 12 | 0/8 | 2/8 | |
| Gemcitabine + CTLA-4 mAb | 120 20 | 8, 12, 16 9, 13, 17 | 112 | >50 | 1/8 | 5/8 | Synergy |

In summary, addition of CTLA-4 mAb to chemotherapeutic agents such as Etoposide, Gemcitabine and Paclitaxel, resulted in synergistic activity supporting the use of chemoimmunotherapy combinations in clinical trials. All the combination regimens were well tolerated. Of note, synergy was observed in tumors that did not respond to CTLA-4 alone suggesting that the chemotherapeutic agents might have induced immunogenic cell death.

The present invention is not limited to the embodiments specifically described above, but is capable of variation and modification without departure from the scope of the appended Claims.

It will be clear that the invention may be practiced otherwise than as particularly described in the foregoing description and examples. Numerous modifications and variations of the present invention are possible in light of the above teachings and, therefore, are within the scope of the appended Claims.

The entire disclosure of each document cited (including patents, patent applications, journal articles, abstracts, laboratory manuals, books, GENBANK® Accession numbers, SWISS-PROT® Accession numbers, or other disclosures) in the Background of the Invention, Detailed Description, Brief Description of the Figures, and Examples is hereby incorporated herein by reference in their entirety. Further, the hard copy of the Sequence Listing submitted herewith, in addition to its corresponding Computer Readable Form, are incorporated herein by reference in their entireties.

What is claimed is:

1. A method for the treatment of cancer, consisting of the administration to a mammal in need thereof a synergistic, therapeutically effective amount of (i) an anti-CTLA-4 antibody, in addition to one or more diluents, vehicles, excipients, and/or inactive ingredients, and (ii) a chemotherapeutic agent, wherein said chemotherapeutic agent is N-(2-chloro-6-methylphenyl)-2-[[6-[4-(2-hydroxyethyl)-1-piperazinyl]-2-methyl-4-pyrimidinyl]amino]-5-thiazolecarboxamide, or a pharmaceutically acceptable salt, solvate, or hydrate thereof, in addition to one or more diluents, vehicles, excipients, and/or inactive ingredients.

2. The method according to claim 1, wherein the anti-CTLA-4 antibody is selected from the group consisting of ipilimumab and tremelimumab.

3. The method according to claim 1, wherein said cancer is a solid tumor.

4. The method according to claim 3, wherein said solid tumor is selected from the group consisting of: lung cancer, pancreatic cancer, prostate cancer, and colon cancer.

5. The method according to claim 1, wherein said method is for the treatment of a tumor refractory to said chemotherapeutic agent.

6. The method according to claim 1, wherein said chemotherapeutic agent is administered concurrently with the administration of said anti-CTLA4 antibody.

7. The method according to claim 1, wherein said chemotherapeutic agent is administered before the administration of said anti-CTLA4 antibody.

8. The method according to claim 1, wherein said chemotherapeutic agent is administered essentially simultaneously with the administration of said anti-CTLA4 antibody.

9. The method according to claim 1, wherein said chemotherapeutic agent is administered daily.

10. The method according to claim 1, wherein said chemotherapeutic agent is administered intermittently for five days followed by two days without treatment.

11. The method according to claim 1, wherein said anti-CTLA4 antibody is administered about every three weeks.

* * * * *

UNITED STATES PATENT AND TRADEMARK OFFICE
CERTIFICATE OF CORRECTION

PATENT NO. : 8,119,129 B2
APPLICATION NO. : 12/462168
DATED : February 21, 2012
INVENTOR(S) : Maria Jure-Kunkel and Francis Y. Lee It is certified that error appears in the above-identified patent and that said Letters Patent is hereby corrected as shown below:

Title Page, Item (54), and Column 1, Line 2
Title, delete "DASATINIB FOR THE" and insert
-- DIVERSE THERAPEUTIC REGIMENS FOR THE SYNERGISTIC --.

Title Page, Column 2
Item (56) (Other Publications)
Line 5, delete "Cargen" insert -- Carden --.

Signed and Sealed this
Sixteenth Day of October, 2012

David J. Kappos
*Director of the United States Patent and Trademark Office*